United States Patent
Karpf et al.

(10) Patent No.: US 11,007,162 B2
(45) Date of Patent: *May 18, 2021

(54) METHODS OF REDUCING SMALL, DENSE LDL PARTICLES

(71) Applicant: CymaBay Therapeutics, Inc., Newark, CA (US)

(72) Inventors: David Karpf, Mountain View, CA (US); Ronald M. Krauss, Berkeley, CA (US); Yun-Jung Choi, Fremont, CA (US); Xueyan Wang, Foster City, CA (US); Francine M. Gregoire, Newton, MA (US)

(73) Assignee: CymaBay Therapeutics, Inc., Newark, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/176,349

(22) Filed: Oct. 31, 2018

(65) Prior Publication Data

US 2019/0298672 A1     Oct. 3, 2019

Related U.S. Application Data

(63) Continuation of application No. 14/995,024, filed on Jan. 13, 2016, now abandoned, which is a continuation of application No. 12/579,996, filed on Oct. 15, 2009, now abandoned.

(60) Provisional application No. 61/106,483, filed on Oct. 17, 2008.

(51) Int. Cl.
    *A61K 31/192*     (2006.01)
    *A61K 31/4015*     (2006.01)
    *A61K 31/09*     (2006.01)

(52) U.S. Cl.
CPC ............ *A61K 31/192* (2013.01); *A61K 31/09* (2013.01); *A61K 31/4015* (2013.01)

(58) Field of Classification Search
None
See application file for complete search history.

(56) References Cited

U.S. PATENT DOCUMENTS

| | | | |
|---|---|---|---|
| 7,301,050 B2 | 11/2007 | Kuo et al. | |
| 9,381,181 B2 | 7/2016 | Roberts et al. | |
| 9,486,428 B2 | 11/2016 | Boudes et al. | |
| 9,616,039 B2 | 4/2017 | Roberts et al. | |
| 10,188,620 B2 * | 1/2019 | Roberts | A61K 31/192 |
| 2003/0220399 A1 | 11/2003 | Luskey et al. | |
| 2005/0033084 A1 | 2/2005 | Daugs | |
| 2005/0124698 A1 | 6/2005 | Kuo et al. | |
| 2006/0014785 A1 | 1/2006 | Zhu et al. | |
| 2006/0058301 A1 | 3/2006 | Zhu et al. | |
| 2006/0058393 A1 | 3/2006 | DeAngelis et al. | |

FOREIGN PATENT DOCUMENTS

| | | |
|---|---|---|
| EP | 1287821 A1 | 3/2003 |
| JP | 2001-354671 A1 | 12/2001 |
| WO | 97/28149 A1 | 8/1997 |
| WO | 01/00603 A1 | 1/2001 |
| WO | 01/79197 A1 | 10/2001 |
| WO | 02/14291 A1 | 2/2002 |
| WO | 02/46154 A1 | 6/2002 |
| WO | 02/50048 A1 | 6/2002 |
| WO | 02/100351 A2 | 12/2002 |
| WO | 2004/092117 A1 | 10/2004 |
| WO | 2005/042478 A2 | 5/2005 |
| WO | 2006/020916 A2 | 2/2006 |
| WO | 2007/033231 A2 | 3/2007 |

OTHER PUBLICATIONS

Hulthe et al. "The Metabolic Syndrome, LDL Particle Size, and Atherosclerosis: The Atherosclerosis and Insulin Resistance (AIR) Study". Arterioscler Thromb Vasc Biol. 2000; 20:2140-2147. (Year: 2000).*
Leibowitz et al. "Activation of PPARDelta Alters Lipid Metabolism in db/db Mice". FEBS Letters. 2000; 473:333-336. (Year: 2000).*
Bays et al., "MBX-8025, A Novel Peroxisome Proliferator Receptor-δ Agonist: Lipid and Other Metabolic Effects in Dyslipidemic Overweight Patients Treated with and without Atorvastatin", J. Clin. Endocrin. Metab., 96(9), 2889-2897 (2011).
Berge et al., "Pharmaceutical Salts", J. Pharm. Sci., 66, 1-19 (1977).
Brown et al., "Identification of peroxisome proliferator-activated receptor ligands from a biased chemical library", Chem. Biol., 4(12), 909-918 (1997).
Choi et al., "Effects of the PPAR-δ agonist MBX-8025 on atherogenic dyslipidemia", Atherosclerosis, 220, 470-476 (2012).
Farnier et al., "Efficacy and safety of the coadministration of ezetimibe with fenofibrate in patients with mixed hyperlipidaemia", Eur. Heart J., 26, 897-905 (2005).
Galeano et al., "Small Dense Low Density Lipoprotein Has Increased Affinity For LDL Receptor-Independent Cell Surface Binding Sites: A Potential Mechanism for Increased Atherogenicity", J. Lipid Res., 39, 1263-1273 (1998).
Lamarche et al., "Small, Dense Low-Density Lipoprotein Particles as a Predictor of teh Risk of Ischemic Heart Disease in Man", Circulation, 95, 67-75 (1997).
Marais, "Therapeutic modulation of low-density lipoprotein size", Curr. Opin. Lipidology, 11(6), 597-602 (2000).
Oliver et al., "A selective peroxisome proliferator-activated receptor δ agonist promotes reverse cholesterol transport", Proc. Nat'l Acad. Sci., 98(9), 5306-5311 (2001).
Packard et al., "The Role of Small, Dense Low Density Lipoprotein (LDL): A New Look", Int. J. Cardiol., 74, S17-S22 (2000).

(Continued)

*Primary Examiner* — Leslie A. Royds Draper
(74) *Attorney, Agent, or Firm* — HDC IP Law, LLP; Sam L. Nguyen

(57) ABSTRACT

The present invention provides methods for increasing LDL particle size.

10 Claims, 11 Drawing Sheets

(56) References Cited

OTHER PUBLICATIONS

Rajman et al., "LDL Particle Size: An Important Drug Target?", Br. J. Clin. Pharmacol., 48, 125-133 (1999).

Reagan-Shaw et al., "Dose translation from animal to human studies revisited", FASEB J., 22, 659-661 (2007).

Risérus et al., "Activation of Peroxisome Proliferator—Activated Receptor (PPAR)δ Promotes Reversal of Multiple Metabolic Abnormalities, Reduces Oxidative Stress, and Increases Fatty Acid Oxidation in Moderately Obese Men", Diabetes, 57, 332-339 (2008).

Sprecher et al., "Triglyceride: High-Density Lipoprotein Cholesterol Effects in Healthy Subjects Administered a Peroxisome Proliferator Activated Receptor δ Agonist", Arterioscler. Thromb. Vasc. Biol., 27, 359-365 (2007).

Wallace et al., "Effects of peroxisome proliferator-activated receptor α/δ agonists on HDL-cholesterol in vervet monkeys", J. Lipid Res., 46, 1009-1016 (2005).

Zhang et al., "Discovery of para-alkylthiophenoxyacetic acids as a novel series of potent and selective PPARδ agonists", Bioorg. Med. Chem. Lett., 17, 3855-3859 (2007).

\* cited by examiner

Effect of Compound II on LDL phenotype changes in 21 days.

Effects on LDL Subclass Concentrations (nmol/L)

METHODS OF REDUCING SMALL, DENSE LDL PARTICLES

CROSS-REFERENCE TO RELATED PATENT APPLICATIONS

This application is a continuation of U.S. application Ser. No. 14/995,024, filed Jan. 13, 2016 and now abandoned, which is a continuation of U.S. application Ser. No. 12/579,996, filed Oct. 15, 2009 and now abandoned. application Ser. No. 12/579,996 claims the benefit of U.S. Provisional Application No. 61/106,483, filed Oct. 17, 2008, which is incorporated by reference for all purposes.

BACKGROUND OF THE INVENTION

The causal relationship between increased levels of low density lipoprotein (LDL) cholesterol and risk of coronary heart disease (CHD) has been well established (Kanel, W. B. et al., Ann Intern Med, 74:1-12 (1971); 4S Trial 1994; Shepherd 1995; WOSCOPS Trial 1998; Sacks 1998; Pedersen 1998)). However, it has long been known that many individuals with elevated LDL cholesterol never experience coronary artery disease (CAD), whereas a significant portion of individuals with premature CAD have normal levels of LDL cholesterol (Kanel, W. B., Am J Cardiol, 76:69C-77C (1995)).

An additional atherogenic risk factor identified in 1982 is LDL particle size and density, which can be used to define specific LDL subclasses in individual subjects (Krauss, R. M. and Burke, D. J., J Lipid Res, 23:97-104 (1982)). In the first population-based case-control study to explore this hypothesis, a predominance of small, dense LDL particles (defining the LDL pattern B) was associated with a 3-fold increase in the risk of myocardial infarction (MI) (Austin, M. A. et al., JAMA, 260:1917-21 (1988)). Subsequently, larger case-control studies found that patients with premature CAD had smaller LDL particle size than controls (Campos, H. et al., Arterioscler Thromb, 12:187-95 (1992)) or both smaller and denser LDL particles than controls (Coresh, J. et al., J Lipid Res, 34:1687-97 (1993). Men with angiographically proven CAD had significantly higher concentrations of small, dense LDL than comparable men without CAD, with an odds ratio of 4.5 (p<0.01); the odds ratio was even higher (6.9, p<0.001) in the men with prior MI compared to the healthy controls (Griffen, B. A. et al., Atherosclerosis, 106:241-53 (1994).

The significant findings from these case-control studies linking the LDL B-pattern (predominance of small, dense LDL) to increased risk of CAD and MI has more recently been confirmed in several large, prospective studies utilizing a nested case-control design, including the Physicians Health Study (Stampfer, M. J. et al., JAMA, 276:882-8 (1996)), the Stanford Five City Project (Gardner, C. D. et al., JAMA, 276:875-81 (1996)), and the Quebec Cardiovascular Study (Lamarche, B. et al., Circulation, 95:69-75 (1997)). A predominance of small, dense LDL is strongly associated with CAD, independently of traditional coronary risk factors (Austin, M. A. et al., JAMA, 260:1917-21 (1988); Austin, M. A. et al., Curr Opin Lipidol, 5:395-403 (1994); Stampfer, M. J. et al., JAMA, 276:882-8 (1996); Bjornheden, T. et al., Atherosclerosis, 123:43-56 (1996); Lamarche, B. et al., Circulation, 95:69-75 (1997); Koba, S. et al., Am Heart J, 144:1026-35 (2002); Moon, J-Y et al., Cardiology, 108:282-289 (2007)). Small, dense LDL has also been shown to be a significant risk factor for premature CAD in women, independent of age, menopausal status, smoking, hypertension, diabetes and LDL cholesterol level (Kamigaki, A. S. et al., Am J Epidemiol, 153(10):939-45 (2001)). Small LDL particle size has also been linked to the risk of developing atherosclerosis as assessed by coronary angiography (Swinkels, D. W. et al., Atherosclerosis, 77:59-67 (1989); Tornvall, P. et al., Atherosclerosis, 90:67-80 (1991); Tornvall, P. et al., Circulation, 88:2180-9 (1993); Rajman, I. et al., Atherosclerosis, 125:231-42 (1996)). Rajman, I. et al., Br J Pharmacol, 48:125-33 (1999)). Therapies that decrease the amount of small, dense LDL and/or increase HDL cholesterol have been shown to reduce the risk of cardiac events (The Coronary Drug Project Research Group, Clofibrate and niacin in coronary heart disease, JAMA, 231:360-81 (1975); Marais, A. D., Curr Opin Lipidol, 11:597-602 (2000); Otvos, J. D. et al., Atherosclerosis, 160:41-8 (2002).

The atherogenicity of small, dense LDL particles appears to result from several potential mechanisms, including: increased susceptibility to oxidation; enhanced vascular permeability; decreased affinity for (and hence, clearance by) the LDL receptor; conformational changes in apo B within small, dense particles; the clear association of this LDL subfraction with insulin resistance/metabolic syndrome; and the association of this LDL pattern with hypertriglyceridemia and low HDL cholesterol levels (Austin, M. A. and Edwards, K. L., Curr Opin Lipid, 7(3):167-71 (1996)). Additionally, the fraction of small, dense LDL particles is strongly correlated with levels of lipoprotein (a) [Lp(a)] (Moon, J-Y et al., Cardiology, 108:282-289 (2007)), a known cardiovascular risk factor (Dahlen, G. H. et al., Circulation, 74:758-65 (1986); Terres, W. et al., Circulation, 91:948-50 (1995); Hahnmann, H. W. et al., Atherosclerosis, 144:221-8 (1999); Uusimaa, P. et al., Heart Vessels, 16:37-41 (2002)). Lp(a) is also correlated with the level of oxidized phospholipids, which may play a role in the pathophysiology of atherosclerosis (Tsimikas, S. et al., J Am Cell Cardiol, 41:360-70 (2003)).

Few currently available drugs significantly increase LDL particle size and decrease LDL particle density. The most widely used class of lipid-lowering agents, the "statins" tend to decrease LDL particle size and increase density, probably due to upregulation of LDL receptors that have a higher affinity toward large, low density LDL particles (Rajman, I. et al., Br J Pharmacol, 48:125-33 (1999)). However, three classes of drugs do appear to reduce the atherogenic small, dense LDL particles. Nicotinic acid clearly lowers small, dense LDL, largely by virtue of reducing triglyceride levels, with only modest reductions in LDL particle diameter in individuals with normal triglyceride levels (Griffen, B. A. et al., Eur J Clin Invest, 22:383-90 (1992); Superko, H. R. and Krauss, R. M., Atherosclerosis, 95:69-76 (1992)). Similarly, the fibrates decrease the level of small, dense LDL particles in patients with combined hyperlipidemia (Tsai, M. Y. et al., Atherosclerosis, 95:35-42 (1992); Bruckert, E. et al., Atherosclerosis, 100:91-102 (1993); Yuan, J. et al., Atherosclerosis, 110:1-11 (1994)), but not in patients with hypercholesterolemia but normal triglyceride levels (Yuan, J. et al., Atherosclerosis, 110:1-11 (1994)). Finally, the thiazoledinediones (TZDs) have consistently demonstrated increases in LDL particle size and decreases in LDL particle density, which appears related to improvements in insulin sensitivity but not to reductions in hypertriglyceridemia (Tack, C. J. J. et al., Diabetes care, 21:796-9 (1998); Freed, M. I. et al., Am J Cardiol, 90:947-52 (2002); Winkler, K. et al., Diabetes Care, 26:2588-94 (2003); Shadid, S. et al., Atherosclerosis, 188:370-6 (2006)).

BRIEF SUMMARY OF THE INVENTION

The present invention provides for methods of decreasing the amount of small, dense LDL particles in a human having LDL particle size pattern I or B. In some embodiments, the method comprises administering a therapeutically-effective amount of a compound of Formula I or a salt, prodrug or isomer thereof to the human wherein the LDL particle size pattern is changed after administration: from pattern I to pattern A; or from pattern B to pattern I or A.

In some embodiments, the human has a lower level of LDL-III particles after the administrating step compared to prior to the administering step. In some embodiments, the human has a lower level of LDL-IV particles after the administrating step compared to prior to the administering step.

In some embodiments, the compound is

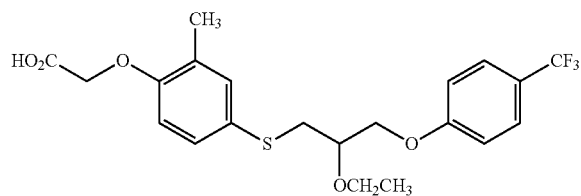

or a salt, prodrug or isomer thereof.

In some embodiments, the compound is

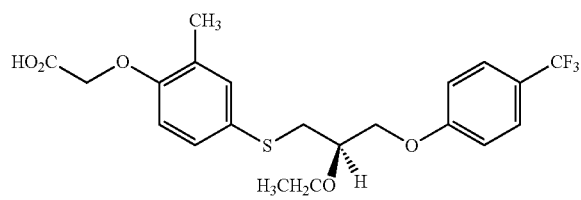

or a salt or prodrug thereof.

In some embodiments, the human has an LDL particle size pattern A after 10 days (e.g., after 20 days, e.g., between 10-100, 10-1000 days) after the administering step. In some embodiments, the human has LDL particle size pattern I after 10 days (e.g., after 20 days, e.g., between 10-100, 10-1000 days) after the administering step. In some embodiments, the method further comprises measuring the LDL particle diameter of the human prior to the administering step. In some embodiments, the method further comprises measuring the LDL particle diameter of the human after the administering step.

In some embodiments, the human has an LDL particle size pattern B prior to the administering step. In some embodiments, the human has an LDL particle size pattern I prior to the administering step.

In some embodiments, the human has diabetes. In some embodiments, the human is insulin resistant. In some embodiments, the human does not have diabetes. In some embodiments, the human has atherosclerosis. In some embodiments, the human has metabolic syndrome. In some embodiments, the human has human has dyslipidemia. In some embodiments, the human does not have atherosclerosis. In some embodiments, the human does not have diabetes. In some embodiments, the human is not insulin resistant. In some embodiments, the human does not have metabolic syndrome. In some embodiments, the human does not have dyslipidemia.

In some embodiments, Apolipoprotein B-100 blood levels are reduced at least 5 or at least 10% or at least 15% or at least 20% after 10 days (e.g., after 20 days, e.g., between 10-100, 10-1000 days) of the administering step. In some embodiments, absorption of cholesterol is reduced by least or at least 10% or at least 15% or at least 20% after 10 days (e.g., after 20 days, e.g., between 10-100, 10-1000 days) of the administering step. In some embodiments, cholesterol synthesis is reduced at least 5% or at least 10% or at least 15% or at least 20% after 10 days (e.g., after 20 days, e.g., between 10-100, 10-1000 days) of the administering step.

In some embodiments, LDL cholesterol blood levels are reduced by at least 15% after 10 days (e.g., after 20 days, e.g., between 10-100, 10-1000 days) of the administering step. In some embodiments, triglyceride blood levels are reduced by at least 20% after 10 days (e.g., after 20 days, e.g., between 10-100, 10-1000 days) of the administering step. In some embodiments, HDL cholesterol blood levels are increased by at least 5% after 10 days (e.g., after 20 days, e.g., between 10-100, 10-1000 days) of the administering step.

The present invention also provides methods of reducing triglycerides and LDL blood levels in a human having LDL particle size pattern I or B. In some embodiments, the method comprises administering a therapeutically-effective amount of a compound of Formula I or a salt, prodrug or isomer thereof to the human wherein the LDL particle size pattern is changed after administration: from pattern I to pattern A; or from pattern B to pattern I or A.

In some embodiments, the compound is

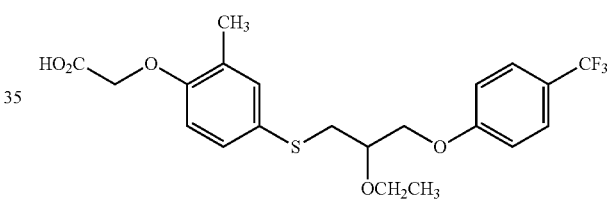

or a salt, prodrug or isomer thereof.

In some embodiments, the compound is

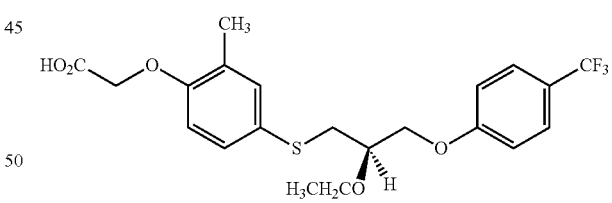

or a salt or prodrug thereof.

In some embodiments, the method further comprises administrating a statin to the human. In some embodiments, the statin is Atorvastatin.

The present invention also provides for methods of identifying a candidate individual for treatment with a compound of Formula I or a salt, prodrug or isomer thereof. In some embodiments, the method comprises measuring the LDL peak particle diameter of an individual; and administering the compound to the individual if the individual had a pattern I or B LDL particle size pattern.

In some embodiments, the individual has a pattern I LDL particle size pattern and the compound is administered to the individual after the measuring step. In some embodiments, the individual has a pattern B LDL particle size pattern and the compound is administered to the individual after the measuring step.

The present invention also provides for therapeutically-effective amount of a compound of Formula I or a salt, prodrug or isomer thereof for use in a human having LDL particle size pattern I or B, wherein the amount is sufficient to change the human's LDL particle size pattern from pattern I to pattern A; or from pattern B to pattern I or A.

In some embodiments, the compound is

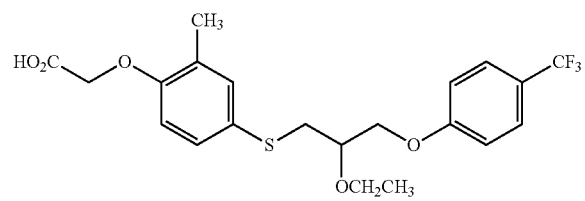 [SMILES: CCOC(COc1ccc(C(F)(F)F)cc1)CSc1ccc(OCC(=O)O)c(C)c1]

or a salt, prodrug or isomer thereof.

In some embodiments, the compound is

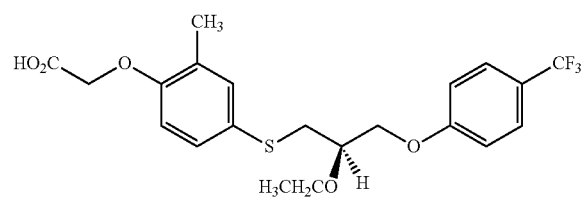

or a salt or prodrug thereof.

In some embodiments, the amount is sufficient such that the human has an LDL particle size pattern A after 10 days after the administering step. In some embodiments, the human has an LDL particle size pattern B prior to the administering step. In some embodiments, the human has an LDL particle size pattern I prior to the administering step.

In some embodiments, the compound is for use in a human who has diabetes. In some embodiments, the compound is for use in a human who is insulin resistant. In some embodiments, the compound is for use in a human who has atherosclerosis. In some embodiments, the compound is for use in a human who has metabolic syndrome. In some embodiments, the compound is for use in a human who has dyslipidemia.

In some embodiments, the amount is sufficient such that Apolipoprotein B-100 blood levels are reduced at least 10% after 10 days of the administering step.

In some embodiments, the amount is sufficient such that absorption of cholesterol is reduced by least 5% after 10 days of the administering step.

In some embodiments, the amount is sufficient such that cholesterol synthesis is reduced at least 5% after 10 days of the administering step.

In some embodiments, the amount is sufficient such that absorption of cholesterol is reduced by least 10% after 10 days of the administering step.

In some embodiments, the amount is sufficient such that cholesterol synthesis is reduced at least 10% after 10 days of the administering step.

In some embodiments, the amount is sufficient such that absorption of cholesterol is reduced by least 20% after 10 days of the administering step.

In some embodiments, the amount is sufficient such that cholesterol synthesis is reduced at least 20% after 10 days of the administering step.

In some embodiments, the amount is sufficient such that LDL cholesterol blood levels are reduced by at least 15% after 10 days of the administering step.

In some embodiments, the amount is sufficient such that triglyceride blood levels are reduced by at least 20% after 10 days of the administering step.

In some embodiments, the amount is sufficient such that HDL cholesterol blood levels are increased by at least 5% after 10 days of the administering step.

The present invention also provides for a method comprising:
a) testing a human for LDL particle size; and
b) providing a therapeutically-effective amount of a compound of Formula I or a salt, prodrug or isomer thereof to the human if the human has LDL particle size pattern I or B, wherein the amount is sufficient to change the human's LDL particle size pattern from pattern I to pattern A; or from pattern B to pattern I or A. "Providing" as used in this context is not intended to refer to administration, but instead encompasses formulation of the drug for the human and/or giving the human the compound (e.g., in pill form) that the human can consume then or later.

In some embodiments, the compound is

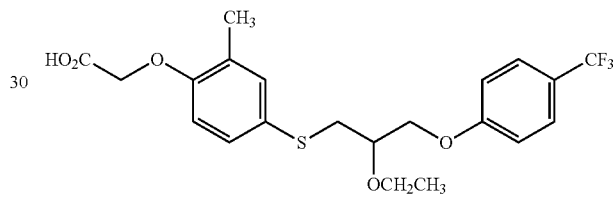

or a salt, prodrug or isomer thereof.

In some embodiments, the compound is

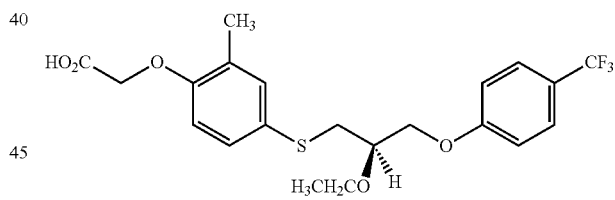

or a salt or prodrug thereof.

In some embodiments, the method further comprises measuring the LDL particle diameter of the human after the providing step and after the human has introduced the compound into the human's body.

In some embodiments, the human has an LDL particle size pattern B prior to the providing step. In some embodiments, the human has an LDL particle size pattern I prior to the providing step.

In some embodiments, the human has diabetes. In some embodiments, the human is insulin resistant. In some embodiments, the human does not have diabetes. In some embodiments, the human has atherosclerosis. In some embodiments, the human has metabolic syndrome. In some embodiments, the human has dyslipidemia.

DEFINITIONS

Figure 1:
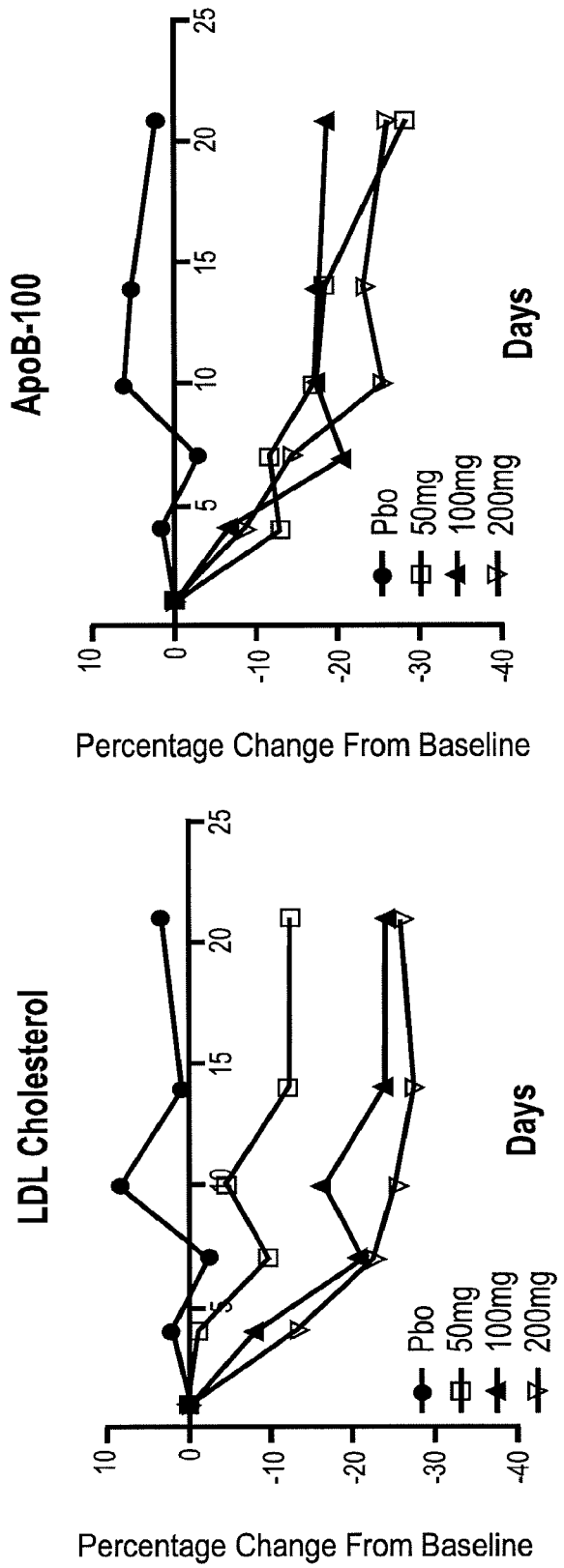
FIG. 1 illustrates the effect of the compound of Formula II on LDL-cholesterol and Apolipoprotein B-100.

"LDL particle diameter" or "LDL particle size" refers to the diameter of LDL particles in blood. See, e.g., Krauss, R M, et al., *J. Lipid. Res.* 23:97-104 (1982); Shen, M M S, et al., *J. Lipid. Res.* 22:235-244 (1981). A variety of methods are known for measuring LDL particle size, including but not limited to, gradient-gel electrophoresis (GGE) and Airborne Ion Mobility (AIM). Particles can be categorized based on their diameter. For example, LDL particles can be divided into four categories (I-IV), where I is the largest particle and IV is the smallest. Using the AIM measurement method, LDL-I corresponds to particles of diameter 21.99-23.80 nm, LDL-II corresponds to particles of diameter 21.10-21.99 nm, LDL-III corresponds to particles of diameter 20.17-21.10 nm, and LDL-IV corresponds to particles of diameter 18.00-20.17 nm. See, e.g., Berneis and Krauss, *J. Lipid Res.* 43:1363-1379 (2002).

In many individuals, one size LDL particle predominates (i.e., is present in the highest amount) compared to LDL particles of other sizes. The predominant LDL particle size can vary between different individuals. Smaller particles are considered risk factors for some diseases including but not limited to coronary disease (see, e.g., Berneis and Krauss, *J. Lipid Res.* 43:1363-1379 (2002)). Individuals with a smaller predominant LDL particle (less than 25.75 nm as measured by GGE) have "pattern B", which are associated with a poorer diagnosis. Individuals with a large predominant LDL particle (greater than 26.34 nm as measured by GGE have "pattern A"). Individuals with a predominant LDL particle size between pattern A and pattern B (i.e., a predominant LDL particle size of 25.75-26.34 nm as measured by GGE) are referred to as having "pattern I."

The term "therapeutically-effective amount" means the amount of the subject compound that will elicit the biological or medical response of a tissue, system, animal or human that is being sought by the researcher, veterinarian, medical doctor or other clinician. A therapeutically effective amount includes the amount of a compound that, when administered to a mammal for treating a disease, is sufficient to effect such treatment for the disease. The therapeutically effective amount will vary depending on the compound, the disease and its severity and the age, weight, etc., of the mammal to be treated.

The term "insulin resistance" can be defined generally as a disorder of glucose metabolism. More specifically, insulin resistance can be defined as the diminished ability of insulin to exert its biological action across a broad range of concentrations producing less than the expected biologic effect (see, e.g., Reaven, G. M., *J. Basic & Clin. Phys. & Pharm.* (1998) 9: 387-406 and Flier, J. *Ann Rev. Med.* (1983) 34: 145-60). Insulin resistant persons have a diminished ability to properly metabolize glucose. Manifestations of insulin resistance include insufficient insulin activation of glucose uptake, oxidation and storage in muscle and inadequate insulin repression of lipolysis in adipose tissue and of glucose production and secretion in liver. Insulin resistance can cause or contribute to polycystic ovarian syndrome, Impaired Glucose Tolerance (IGT), gestational diabetes, hypertension, obesity, hypertriglyceridemia, atherosclerosis and a variety of other disorders. Eventually, the insulin resistant individuals can progress to a point where a diabetic state is reached. The association of insulin resistance with glucose intolerance, an increase in plasma triglyceride and a decrease in high-density lipoprotein cholesterol concentrations, high blood pressure, hyperuricemia, smaller denser low-density lipoprotein particles, and higher circulating levels of plaminogen activator inhibitor-1, has been referred to as "Syndrome X" (see, e.g., Reaven, G. M., *Physiol. Rev.* (1995) 75: 473-486), also known as "metabolic syndrome."

"Insulin sensitivity" refers to the ability of a cell or tissue to respond to insulin. Individuals having insulin resistance have reduced insulin sensitivity compared to healthy lean individuals. Responses include, e.g., glucose uptake of a cell or tissue in response to insulin stimulation. Sensitivity can be determined at an organismal, tissue or cellular level. For example, blood or urine glucose levels following a glucose tolerance test are indicative of insulin sensitivity. Other methods of measuring insulin sensitivity include, e.g., measuring glucose uptake (see, e.g., Garcia de Herreros, A., and Birnbaum, M. J. *J. Biol. Chem.* 264, 19994-19999 (1989); Klip, A., Li, G., and Logan, W. J. *Am. J. Physiol.* 247, E291-296 (1984)), measuring the glucose infusion rate (GINF) into tissue such as the skeletal muscle (see, e.g., Ludvik et al., *J Clin. Invest.* 100:2354 (1997); Frias et al., *Diabetes Care* 23:64, (2000)) and measuring sensitivity of GLUT4 translocation in response to insulin.

The term "diabetes mellitus" or "diabetes" means a disease or condition that is generally characterized by metabolic defects in production and utilization of glucose which result in the failure to maintain appropriate blood sugar levels in the body. The result of these defects is elevated blood glucose, referred to as "hyperglycemia." Two major forms of diabetes are Type 1 diabetes and Type 2 diabetes. As described above, Type 1 diabetes is generally the result of an absolute deficiency of insulin, the hormone which regulates glucose utilization. Type 2 diabetes often occurs in the face of normal, or even elevated levels of insulin and can result from the inability of tissues to respond appropriately to insulin. Most Type 2 diabetic patients are insulin resistant and have a relative deficiency of insulin, in that insulin secretion can not compensate for the resistance of peripheral tissues to respond to insulin. In addition, many but not all Type 2 diabetics are obese. Other types of disorders of glucose homeostasis include Impaired Glucose Tolerance, which is a metabolic stage intermediate between normal glucose homeostasis and diabetes, and Gestational Diabetes Mellitus, which is glucose intolerance in pregnancy in women with no previous history of Type 1 or Type 2 diabetes.

The terms "obese" and "obesity" refers to, according to the World Health Organization, a Body Mass Index (BMI) greater than 27.8 kg/m² for men and 27.3 kg/m² for women (BMI equals weight (kg)/height (m²). Obesity is linked to a variety of medical conditions including diabetes and hyperlipidemia. Obesity is also a known risk factor for the development of Type 2 diabetes (See, e.g., Barrett-Conner, E., *Epidemol. Rev.* (1989) 11: 172-181; and Knowler, et al., *Am. J. Clin. Nutr.* (1991) 53:1543-1551).

Unless otherwise noted, as used herein and whether used alone or as part of a substituent group, "alkyl" and "alkoxy" include straight and branched chains having 1 to 8 carbon atoms, such as $C_{1-6}$, $C_{1-4}$, $C_{3-8}$, $C_{2-5}$, or any other range, and unless otherwise noted, include both substituted and unsubstituted moieties. For example, $C_{1-6}$alkyl radicals include methyl, ethyl, n-propyl, isopropyl, n-butyl, isobutyl, sec-butyl, t-butyl, n-pentyl, 3-(2-methyl)butyl, 2-pentyl, 2-methylbutyl, neopentyl, n-hexyl, 2-hexyl and 2-methylpentyl. Alkoxy radicals are formed from the previously described straight or branched chain alkyl groups. "Alkyl" and "alkoxy" include unsubstituted or substituted moieties with one or more substitutions, such as between 1 and 5, 1 and 3, or 2 and 4 substituents. The substituents may be the same (dihydroxy, dimethyl), similar (chloro, fluoro), or different (chlorobenzyl- or aminomethyl-substituted). Examples of substituted alkyl include haloalkyl (such as fluoromethyl, chloromethyl, difluoromethyl, perchloromethyl, 2-bromoethyl, trifluoromethyl, and 3-iodocyclopentyl), hydroxyalkyl (such as hydroxymethyl, hydroxyethyl, 2-hydroxypropyl), aminoalkyl (such as aminomethyl, 2-aminoethyl, 3-aminopropyl, and 2-aminopropyl), alkoxylalkyl, nitroalkyl, alkylalkyl, cyanoalkyl, phenylalkyl, heteroarylalkyl, heterocyclylalkyl, phenoxyalkyl, heteroaryloxyalkyl (such as 2-pyridyloxyalkyl), heterocyclyloxy-alkyl (such as 2-tetrahydropyranoxy-alkyl), thioalkylalkyl (such as MeS-alkyl), thiophenylalkyl (such as phS-alkyl), carboxylalkyl, and so on. A di($C_{1-3}$alkyl)amino group includes independently selected alkyl groups, to form, for example, methylpropylamino and isopropylmethylamino, in addition dialkylamino groups having two of the same alkyl group such as dimethyl amino or diethylamino.

The term "alkenyl" includes optionally substituted straight chain and branched hydrocarbon radicals as above with at least one carbon-carbon double bond ($sp_2$). Alkenyls include ethenyl (or vinyl), prop-1-enyl, prop-2-enyl (or allyl), isopropenyl (or 1-methylvinyl), but-1-enyl, but-2-enyl, butadienyls, pentenyls, hexa-2,4-dienyl, and so on. Hydrocarbon radicals having a mixture of double bonds and triple bonds, such as 2-penten-4-ynyl, are grouped as alkynyls herein. Alkenyl includes cycloalkenyl. Cis and trans or (E) and (Z) forms are included within the invention. "Alkenyl" may be substituted with one or more substitutions including, but not limited to, cyanoalkenyl, and thioalkenyl.

The term "alkynyl" includes optionally substituted straight chain and branched hydrocarbon radicals as above with at least one carbon-carbon triple bond (sp). Alkynyls include ethynyl, propynyls, butynyls, and pentynyls. Hydrocarbon radicals having a mixture of double bonds and triple bonds, such as 2-penten-4-ynyl, are grouped as alkynyls herein. Alkynyl does not include cycloalkynyl.

The term "Ac" as used herein, whether used alone or as part of a substituent group, means acetyl ($CH_3CO$—).

The term "halogen" or "halo" shall include iodo, bromo, chloro and fluoro.

The terms "aryl" or "Ar" as used herein refer to an unsubstituted or substituted aromatic hydrocarbon ring system such as phenyl and naphthyl. When the Ar or aryl group is substituted, it may have one to three substituents which are independently selected from $C_1$-$C_8$ alkyl, $C_1$-$C_8$ alkoxy, fluorinated $C_1$-$C_8$ alkyl (e.g., trifluoromethyl), fluorinated $C_1$-$C_8$ alkoxy (e.g., trifluoromethoxy), halogen, cyano, C1-C8 alkylcarbonyl such as acetyl, carboxyl, hydroxy, amino, nitro, $C_1$-$C_4$ alkylamino (i.e., —NH—$C_1$-$C_4$ alkyl), $C_1$-$C_4$ dialkylamino (i.e., —N—[$C_1$-$C_4$ alkyl]$_2$ wherein the alkyl groups can be the same or different), or unsubstituted, mono-, di- or tri-substituted phenyl wherein the substituents on the phenyl are independently selected from $C_1$-$C_8$ alkyl, $C_1$-$C_8$ alkoxy, fluorinated $C_1$-$C_8$ alkyl, fluorinated $C_1$-$C_8$ alkoxy, halogen, cyano, acetyl, carboxyl, hydroxy, amino, nitro, alkylamino, dialkylamino or five or six membered heteroaryl having 1-3 heteroatoms selected from N, O and S.

The term "heteroaryl" as used herein represents a stable, unsubstituted or substituted five or six membered monocyclic or bicyclic aromatic ring system which consists of carbon atoms and from one to three heteroatoms selected from N, O and S. The heteroaryl group may be attached at any heteroatom or carbon atom which results in the creation of a stable structure. Examples of heteroaryl groups include, but are not limited to, benzimidazolyl, benzisoxazolyl, benzofuranyl, benzopyrazolyl, benzothiadiazolyl, benzothiazolyl, benzothienyl, benzotriazolyl, benzoxazolyl, furanyl, furazanyl, furyl, imidazolyl, indazolyl, indolizinyl, indolinyl, indolyl, isobenzofuranyl, isoindolyl, isothiazolyl, isoxazolyl, oxazolyl, purinyl, pyrazinyl, pyrazolyl, pyridazinyl, pyridinyl, pyrimidinyl, pyrrolyl, quinolinyl, quinolyl, thiadiazolyl, thiazolyl, thiophenyl, or triazolyl. When the heteroaryl group is substituted, the heteroaryl group may have one to three substituents including, but not limited to, $C_1$-$C_8$ alkyl, halogen, and aryl.

The term "heterocyclyl" includes optionally substituted nonaromatic rings having carbon atoms and at least one heteroatom (O, S, N) or heteroatom moiety ($SO_2$, CO, CONH, COO) in the ring. A heterocyclyl may be saturated, partially saturated, nonaromatic, or fused. Examples of heterocyclyl include cyclohexylimino, imdazolidinyl, imidazolinyl, morpholinyl, piperazinyl, piperidyl, pyridyl, pyranyl, pyrazolidinyl, pyrazolinyl, pyrrolidinyl, pyrrolinyl, and thienyl.

Unless otherwise indicated, heteroaryl and heterocyclyl may have a valence connecting it to the rest of the molecule through a carbon atom, such as 3-furyl or 2-imidazolyl, or through a heteroatom, such as N-piperidyl or 1-pyrazolyl. Preferably a monocyclic heterocyclyl has between 5 and 7 ring atoms, or between 5 and 6 ring atoms; there may be between 1 and 5 heteroatoms or heteroatom moieties in the ring, and preferably between 1 and 3, or between 1 and 2 heteroatoms or heteroatom moieties.

Heterocyclyl and heteroaryl also include fused, e.g., bicyclic, rings, such as those optionally fused with an optionally substituted carbocyclic or heterocyclic five- or six-membered aromatic ring. For example, "heteroaryl" includes an optionally substituted six-membered heteroaromatic ring containing 1, 2 or 3 nitrogen atoms fused with an optionally substituted five- or six-membered carbocyclic or heterocyclic aromatic ring. Said heterocyclic five- or six-membered aromatic ring fused with the said five- or six-membered aromatic ring may contain 1, 2 or 3 nitrogen atoms where it is a six-membered ring, or 1, 2 or 3 heteroatoms selected from oxygen, nitrogen and sulfur where it is a five-membered ring.

It is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques known in the art as well as those methods set forth herein.

Where chemical moieties are combined, such as in ethoxymethyl or phenylethyl, the term is described in the direction from the periphery to the connection point of the rest of the molecule. For example, ethoxymethyl is $CH_3CH_2OCH_2$— and phenylethyl is a phenyl group linked by —$CH_2CH_2$— to the rest of the molecule (and not a phenyl group linked to the molecule with a $CH_3CH_2$ group as a substituent on the phenyl.) Where parentheses are used, they indicate a peripheral substitution.

DETAILED DESCRIPTION OF THE INVENTION

I. Introduction

The present invention is based, in part, on the surprising discovery that a PPAR delta agonist of the present invention is effective in decreasing the amount of small, dense LDL particles in the blood in humans. Notably, nearly all patients treated with the compound displayed a significantly improved LDL particle distribution. Indeed, in an initial study, after treatment with 100 or 200 mg doses, every patient treated with the compound had a LDL subclass pattern A (i.e., a peak LDL particle diameter of greater than 263.4 Å), whereas before treatment, the patients were a mixture of patterns A, I (between 263.4 and 257.5 Å) and B (less than 257.5 Å). Further, both LDL-cholesterol and Apolipoprotein B-100 levels decreased in patients treated with the compound, while HDL levels increased. In view of this data, the compounds of the invention find particular benefit in individuals having a small predominant LDL particle size (e.g., pattern B or I).

II. Compounds of the invention

The present invention allows for methods of decreasing the number of small, dense LDL particles in a human, as well as methods of lowering the levels of Apolipoprotein B-100, LDL-cholesterol and triglycerides, increasing levels of HDL-cholesterol and inhibiting cholesterol synthesis and adsorption, as described herein, using a PPAR delta agonist. A wide variety of PPAR delta agonists are known, including, but not limited to, those disclosed below.

Compounds that are known to be selective PPAR delta are known in the art, including, e.g., the compound known as GW501516, e.g., as described in WO 01/00603, and the compound known as L-165,041, e.g., as disclosed in European Patent Application 28063 and in WO 97/28149.

Other than L-165016 and GW501516, numerous compounds have been reported in, e.g., WO2002100351, WO0200250048, WO0179197, WO0246154, WO0214291 and Japanese Patent Application No. 2001-354671 as agonists with relatively high activity to the subtype PPARδ. Additionally, Brown P J et al. report compounds for example GW2433 (Brown P J, et al., *Chem. Biol.* 909-918 (1997)).

It will be appreciated that additional PPAR delta agonists can be identified in screening methods, including but not limited to the methods described in US Patent Publication No. 20070037882, and the references cited therein.

In some embodiments, the invention features PPAR delta agonists that are compounds of Formula (I) below:

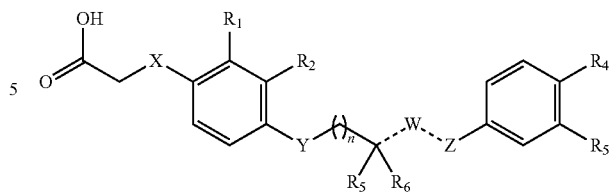

wherein

X is selected from a covalent bond, S, or O;

Y is S or O;

- - - W - - - represents a group selected from ═CH—, —H═, —$CH_2$—, —$CH_2$—$CH_2$, ═CH—$CH_2$, —$CH_2$CH, —CH═CH═, and —CH═CH—;

Z is selected from O, CH, and $CH_2$, provided when Y is O, Z is O;

$R_1$ and $R_2$ are independently selected from H, $C_{1-3}$alkyl, $C_{1-3}$alkoxy, halo, and $NR_aR_b$, wherein $R_a$ and $R_b$ are independently H or $C_{1-3}$alkyl;

$R_3$ and $R_4$ are independently selected from H, halo, cyano, hydroxy, acetyl, $C_{1-5}$alkyl, $C_{1-4}$alkoxy, and $NR_cR_d$ wherein $R_c$ and $R_d$ are independently H or $C_{1-3}$alkyl, provided that $R_3$ and $R_4$ are not both H;

$R_5$ is selected from halo, phenyl, phenoxy, (phenyl)$C_{1-5}$ alkoxy, (phenyl)$C_{1-5}$alkyl, $C_{2-5}$heteroaryloxy, $C_{2-5}$heteroaryl$C_{1-5}$alkoxy. $C_{2-5}$heterocyclyloxy, $C_{1-9}$alkoxy, $C_{1-8}$ alkoxy, $C_{2-9}$alkenyl, $C_{2-9}$alkenyloxy, $C_{2-9}$alkynyl, $C_{2-9}$alkynyloxy, $C_{3-7}$cycloalkyl, $C_{3-7}$cycloalkoxy, $C_{3-7}$cycloalkyl-$C_{1-7}$alkyl, $C_{3-7}$cycloalkyl-$C_{1-7}$alkoxy, $C_{3-7}$cycloalkyloxy-$C_{1-6}$alkyl, $C_{1-6}$alkoxy-$C_{1-6}$alkyl, $C_{1-5}$alkoxy-$C_{1-5}$alkoxy, or $C_{3-7}$cycloalkyloxy-$C_{1-7}$ alkoxy;

$R_6$ is H when - - - W - - - represents a group selected from —CH═, —$CH_2$, —$CH_2$—$CH_2$, —$CH_2$—CH═, and —CH═CH—, or R6 is absent where - - - W - - - represents a group selected from ═CH—, ═CH—CH2, and ═CH—CH═; and n is 1 or 2;

or a pharmaceutically acceptable salt thereof.

Numerous examples of exemplary compounds within the scope of Formula I, as well as synthetic pathways for generating such compounds, are described in, e.g., U.S. Pat. No. 7,301,050, which is incorporated by reference. For example, the present invention encompasses each of the compounds disclosed in Table 1 of U.S. Pat. No. 7,301,050.

In some embodiments, the compounds used in the methods of the invention is the compound shown in Formula II:

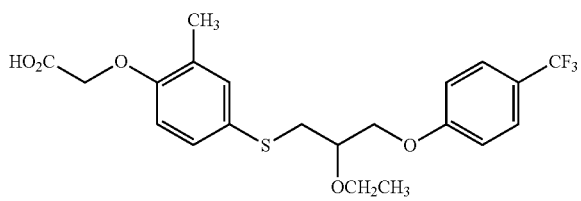

or a salt, prodrug or isomer thereof. In some embodiments, the compound is

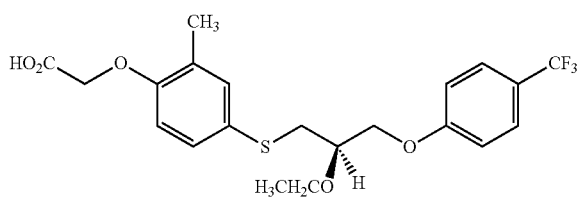

or a salt, prodrug or isomer thereof.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

The invention provides the disclosed compounds and closely related, pharmaceutically acceptable forms of the disclosed compounds, such as salts, esters, amides, hydrates or solvated forms thereof; masked or protected forms; and racemic mixtures, or enantiomerically or optically pure forms.

Pharmaceutically acceptable salts, esters, and amides include carboxylate salts (e.g., $C_{1-8}$ alkyl, cycloalkyl, aryl, heteroaryl, or non-aromatic heterocyclic)amino acid addition salts, esters, and amides which are within a reasonable benefit/risk ratio, pharmacologically effective and suitable for contact with the tissues of patients without undue toxicity, irritation, or allergic response. Representative salts include hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate, and laurylsulfonate. These may include alkali metal and alkali earth cations such as sodium, potassium, calcium, and magnesium, as well as non-toxic ammonium, quaternary ammonium, and amine cations such as tetramethyl ammonium, methylamine, trimethylamine, and ethylamine. See e.g., S. M. Berge, et al., "Pharmaceutical Salts," *J. Pharm. Sci.*, 1977, 66:1 19, which is incorporated herein by reference. Representative pharmaceutically acceptable amides of the invention include those derived from ammonia, primary $C_{1-6}$ alkyl amines and secondary di($C_{1-6}$ alkyl)amines. Secondary amines include 5- or 6-membered heterocyclic or heteroaromatic ring moieties containing at least one nitrogen atom and optionally between 1 and 2 additional heteroatoms. Preferred amides are derived from ammonia, $C_{1-3}$ alkyl primary amines, and di($C_{1-2}$ alkyl)amines. Representative pharmaceutically acceptable esters of the invention include $C_{1-7}$ alkyl, $C_{5-7}$ cycloalkyl, phenyl, and phenyl($C_{1-6}$) alkyl esters. In some embodiments, the esters are methyl esters.

The invention also includes disclosed compounds having one or more functional groups (e.g., amino, or carboxyl) masked by a protecting group. Some of these masked or protected compounds are pharmaceutically acceptable; others will be useful as intermediates. Synthetic intermediates and processes (e.g., as disclosed in U.S. Pat. No. 7,301,050), and minor modifications thereof, are also within the scope of the invention.

Hydroxyl Protecting Groups

Protection for the hydroxyl group includes methyl ethers, substituted methyl ethers, substituted ethyl ethers, substitute benzyl ethers, and silyl ethers.

Substituted Methyl Ethers

Examples of substituted methyl ethers include methyoxymethyl, methylthiomethyl, t-butylthiomethyl, (phenyldimethylsilyl)methoxymethyl, benzyloxymethyl, p-methoxybenzyloxymethyl, (4-methoxyphenoxy)methyl, guaiacolmethyl, t-butoxymethyl, 4-pentenyloxymethyl, siloxymethyl, 2-methoxyethoxymethyl, 2,2,2-trichloroethoxymethyl, bis(2-chloroethoxy)methyl, 2-(trimethylsilyl)ethoxymethyl, tetrahydropyranyl, 3-bromotetrahydropyranyl, tetrahydrothiopyranyl, 1-methoxycyclohexyl, 4-methoxytetrahydropyranyl, 4-methoxytetrahydrothiopyranyl, 4-methoxytetrahydrothiopyranyl S,S-dioxido, 1-[(2-chloro-4-methyl)phenyl]4-methoxypiperidin-4-yl, 1,4-dioxan-2-yl, tetrahydropyranyl, tetrahydrothiofuranyl and 2,3, 3a,4,5,6,7,7a-octahydro-7,8,8-trimethyl-4,7-methanobenzofuran-2-yl.

Substituted Ethyl Ethers

Examples of substituted ethyl ethers include 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, and benzyl.

Substituted Benzyl Ethers

Examples of substituted benzyl ethers include p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2- and 4-picolyl, 3-methyl-2-picolyl N-oxide, diphenylmethyl, p,p'-dinitrobenzhydryl, 5-dibenzosuberyl, triphenylmethyl, .alpha.-naphthyldiphenylmethyl, p-methoxyphenyldiphenylmethyl, di(p-methoxyphenyl)phenylmethyl, tri(p-methoxyphenyl)methyl, 4-(4'-bromophenacyloxy)phenyldiphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-ylmethyl)bis(4', 4"dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, and benzisothiazolyl S,S-dioxido.

Silyl Ethers

Examples of silyl ethers include trimethylsilyl, triethylsilyl, triisopropylsilyl, dimethylisopropylsilyl, diethylisopropylsilyl, dimethylthexylsilyl, t-butyldimethylsilyl, t-butyldiphenylsilyl, tribenzylsilyl, tri-p-xylylsilyl, triphenylsilyl, diphenylmethylsilyl, and t-butylmethoxyphenylsilyl.

Esters

In addition to ethers, a hydroxyl group may be protected as an ester. Examples of esters include formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, p-P-phenylacetate, 3-phenylpropionate, 4-oxopentanoate (levulinate), 4,4-(ethylenedithio)pentanoate, pivaloate, adamantoate, crotonate, 4-methoxycrotonate, benzoate, p-phenylbenzoate, 2,4,6-trimethylbenzoate (mesitoate)

Carbonates

Examples of carbonates include methyl, 9-fluorenylmethyl, ethyl, 2,2,2-trichloroethyl, 2-(trimethylsilyl)ethyl, 2-(phenylsulfonyl)ethyl, 2-(triphlenylphosphonio)ethyl, isobutyl, vinyl, allyl, p-nitrophenyl; benzyl, p-methoxybenzyl, 3,4-dimethoxybenzyl, o-nitrobenzyl, p-nitrobenzyl, S-benzyl thiocarbonate, 4-ethoxy-1-naphthyl, and methyl dithiocarbonate.

Assisted Cleavage

Examples of assisted cleavage include 2-iodobenzoate, 4-azidobutyrate, 4-nitro-4-methylpentanoate, o-(dibromomethyl)benzoate, 2-formylbenzenesulfonate, 2-(methylthiomethoxy)ethyl carbonate, 4-(methylthiomethoxy)butyrate, and 2-(methylthiomethoxymethyl)benzoate.

Miscellaneous Esters

Examples of miscellaneous esters include 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate (tigloate), o-(methoxycarbonyObenzoate, p-P-benzoate, α-naphthoate, nitrate, alkyl N,N,N',N'-tetramethylphosphorodiamidate, N-phenylcarbamate, borate, dimethylphosphinothioyl, and 2,4-dinitrophenylsulfenate.

Sulfonates

Examples of sulfonates include sulfate, methanesulfonate (mesylate), benzylsulfonate, and tosylate.

Amino Protecting Groups

Protection for the amino group includes carbamates, amides, and special —NH protective groups.

Examples of carbamates include methyl and ethyl carbamates, substituted ethyl carbamates, assisted cleavage carbamates, photolytic cleavage carbamates, urea-type derivatives, and miscellaneous carbamates.

Carbamates

Examples of methyl and ethyl carbamates include methyl and ethyl, 9-fluorenylmethyl, 9-(2-sulfo)fluorenylmethyl, 9-(2,7-dibromo)fluorenylmethyl, 2,7-di-t-butyl-[9(10,10-dioxo-10,10,10,10-tetrahydrothioxanthyl)]methyl, and 4-methoxyphenacyl.

Substituted Ethyl

Examples of substituted ethyl carbamates include 2,2,2-trichloroethyl, 2-trimethylsilylethyl, 2-phenylethyl, 1-(1-adamantyl)-1-methylethyl, 1,1-dimethyl-2-haloethyl, 1,1-dimethyl-2,2-dibromoethyl, 1,1-dimethyl-2,2,2-trichloroethyl, 1-methyl-1-(4-biphenylyl)ethyl, 1-(3,5-di-t-butylphenyl)-1-methylethyl, 2-(2'- and 41-pyridyl)ethyl, 2-(N,N-dicyclohexylcarboxamido)ethyl, t-butyl, 1-adamantyl, vinyl, allyl, 1-isopropylallyl, cinnamyl, 4-nitrocinnamyl, 8-quinolyl, N-hydroxypiperidinyl, alkyldithio, benzyl, p-methoxybenzyl, p-nitrobenzyl, p-bromobenzyl, p-chlorobenzyl, 2,4-dichlorobenzyl, 4-methylsulfinylbenzyl, 9-anthrylmethyl and diphenylmethyl.

Assisted Cleavage

Examples of assisted cleavage include 2-methylthioethyl, 2-methylsulfonylethyl, 2-(p-toluenesulfonyl)ethyl, [2-(1,3-dithianyl)]methyl, 4-methylthiophenyl, 2,4-dimethylthiophenyl, 2-phosphonioethyl, 2-triphenylphosphonioisopropyl, 1,1-dimethyl-2-cyanoethyl, m-chloro-p-acyloxybenzyl, p-(dihydroxyboryl)benzyl, 5-benzisoxazolylmethyl, and 2-(trifluoromethyl)-6-chromonylmethyl.

Photolytic Cleavage

Examples of photolytic cleavage include m-nitrophenyl, 3,5-dimethoxybenzyl, o-nitrobenzyl, 3,4-dimethoxy-6-nitrobenzyl, and phenyl(o-nitrophenyl)methyl.

Urea-Type Derivatives

Examples of urea-type derivatives include phenothiazinyl-(10)-carbonyl derivative, N'-p-toluenesulfonylaminocarbonyl, and N'-phenylaminothiocarbonyl.

Miscellaneous Carbamates

Examples of miscellaneous carbamates include t-amyl, S-benzyl thiocarbamate, p-cyanobenzyl, cyclobutyl, cyclohexyl, cyclopentyl, cyclopropylmethyl, p-decyloxybenzyl, diisopropylmethyl, 2,2-dimethoxycarbonylvinyl, o-(N,N-dimethylcarboxamido)benzyl, 1,1-dimethyl-3-(N,N-dimethylcarboxamido)propyl, 1,1-dimethylpropynyl, di(2-pyridyl)methyl, 2-furanylmethyl, 2-iodoethyl, isobornyl, isobutyl, isonicotinyl, p-(p'-methoxyphenylazo)benzyl, 1-methylcyclobutyl, 1-methylcyclohexyl, 1-methyl-1-cyclopropylmethyl, 1-methyl-1-(3,5-dimethoxyphenyl)ethyl, 1-methyl-1-(p-phenylazophenyl)ethyl, 1-methyl-1-phenylethyl, 1-methyl-1-(4-pyridyl)ethyl, phenyl, p-(phenylazo)benzyl, 2,4,6-tri-t-butylphenyl, 4-(trimethylammonium)benzyl, and 2,4,6-trimethylbenzyl.

Examples of amides include:

Amides

N-formyl, N-acetyl, N-chloroacetyl, N-trichloroacetyl, N-trifluoroacetyl, N-phenylacetyl, N-3-phenylpropionyl, N-picolinoyl, N-3-pyridylcarboxamide, N-benzoylphenylalanyl derivative, N-benzoyl, N-p-phenylbenzoyl.

Assisted Cleavage

N-o-nitrophenylacetyl, N-o-nitrophenoxyacetyl, N-acetoacetyl, (N'-dithiobenzyloxycarbonylamino)acetyl, N-3-(p-hydroxyphenyl)propionyl, N-3-(o-nitrophenyl)propionyl, N-2-methyl-2-(o-nitrophenoxy)propionyl, N-2-methyl-2-(o-phenylazophenoxy)propionyl, N-4-chlorobutyryl, N-3-methyl-3-nitrobutyryl, N-o-nitrocinnamoyl, N-acetylmethionine derivative, N-o-nitrobenzoyl, N-o-(benzoyloxymethyl)benzoyl, and 4,5-diphenyl-3-oxazolin-2-one.

Cyclic Imide Derivatives

N-phthalimide, N-dithiasuccinoyl, N-2,3-diphenylmaleoyl, N-2,5-dimethylpyrrolyl, N-1,1,4,4-tetramethyldisilylazacyclopentane adduct, 5-substituted 1,3-'dimethyl-'1,3,5-triazacyclohexan-2-one, 5-substituted 1,3-dibenzyl-1,3,5-triazacyclohexan-2-one, and 1-substituted 3,5-dinitro-4-pyridonyl.

Special—NH Protective Groups

Examples of special NH protective groups include:

N-Alkyl and N-Aryl Amines

N-methyl, N-allyl, N-[2-(trimethylsilyl)ethoxy]methyl, N-3-acetoxypropyl, N-(1-isopropyl-4-nitro-2-oxo-3-pyrrolin-3-yl), quaternary ammonium salts, N-benzyl, N-di(4-methoxyphenyl)methyl, N-5-dibenzosuberyl, N-triphenyl methyl, N-(4methoxyphenyl)diphenylmethyl, N-9-phenylfluorenyl, N-2,7-dichloro-9-fluorenylmethylene, N-ferrocenylmethyl, and N-2-picolylamine N'-oxide.

Imine Derivatives

N-1,1-dimethylthiomethylene, N-benzylidene, N-p-methoxybenzylidene, N-diphenylmethylene, N-[(2-pyridyl)mesityl]methylene, and N—(N',N'-dimethylaminomethylene).

Protection for the Carboxyl Group Esters

Examples of esters include formate, benzoylformate, acetate, trichloroacetate, trifluoroacetate, methoxyacetate, phenoxyacetate, p-chlorophenoxyacetate, benzoate.

Substituted Methyl Esters

Examples of substituted methyl esters include 9-fluorenylmethyl, methoxymethyl, methylthiomethyl, tetrahydropyranyl, tetrahydrofuranyl, methoxyethoxymethyl, 2-(trimethylsilyl)ethoxymethyl, benzyloxymethyl, phenacyl, p-bromophenacyl, .alpha.-methylphenacyl, p-methoxyphenacyl, carboxamidomethyl, and N-phthalimidomethyl.

2-Substituted Ethyl Esters

Examples of 2-substituted ethyl esters include 2,2,2-trichloroethyl, 2-haloethyl, (.omega.-chloroalkyl, 2-(trimethylsilyl)ethyl, 2-methylthioethyl, 1,3-dithianyl-2-methyl, 2-(p-nitrophenylsulfenyl)ethyl, 2-(p-toluenesulfonyl)ethyl, 2-(T-pyridyl)ethyl, 2-(diphenylphosphino)ethyl, 1-methyl-1-phenylethyl, t-butyl, cyclopentyl, cyclohexyl, allyl, 3-buten-1-yl, 4-(trimethylsilyl)-2-buten-1-yl, cinnamyl, .alpha.-methylcinnamyl, phenyl, p-(methylmercapto)phenyl and benzyl.

Substituted Benzyl Esters

Examples of substituted benzyl esters include triphenylmethyl, diphenylmethyl, bis(o-nitrophenyl)methyl, 9-anthrylmethyl, 2-(9,10-dioxo)anthrylmethyl, 5-dibenzosuberyl, 1-pyrenylmethyl, 2-(trifluoromethyl)-6-chromylmethyl, 2,4,6trimethylbenzyl, p-bromobenzyl, o-nitrobenzyl, p-nitrobenzyl, p-methoxybenzyl, 2,6-dimethoxybenzyl, 4-(methylsulfinyl)benzyl, 4-sulfobenzyl, piperonyl, 4-picolyl and p-P-benzyl.

Silyl Esters

Examples of silyl esters include trimethylsilyl, triethylsilyl, t-butyldimethylsilyl, i-propyldimethylsilyl, phenyldimethylsilyl and di-t-butylmethylsilyl.

Activated Esters

Examples of activated esters include thiols.

Miscellaneous Derivatives

Examples of miscellaneous derivatives include oxazoles, 2-alkyl-1,3-oxazolines, 4-alkyl-5-oxo-1,3-oxazolidines, 5-alkyl-4-oxo-1,3-dioxolanes, ortho esters, phenyl group and pentaaminocobalt (III) complex.

Stannyl Esters

Examples of stannyl esters include triethylstannyl and tri-n-butylstannyl.

Methods for synthesizing the compounds of Formula I have been described previously, for example, in U.S. Pat. No. 7,301,050.

III. Patient Populations

As demonstrated in the data provided herein, certain classes of individuals derive a particularly significant benefit from receiving a PPAR delta agonist such as those set forth in Formula I and as described herein. Those deriving a particularly significant benefit include those individuals with a predominant LDL particle that is small (e.g., pattern B or I), those with a high Apolipoprotein B-100 blood level and/or those with high triglycerides and/or cholesterol. As shown in the data presented herein, surprisingly it has been found that compounds of the present invention are effective in addressing each of the above-listed risk factors, i.e., by significantly decreasing the amount of small LDL particles, reducing blood levels of Apolipoprotein B-100, LDL cholesterol, and triglycerides, raising blood levels of HDL cholesterol, and by blocking both cholesterol synthesis and absorption.

Accordingly, in some embodiments, a compound of the present invention is administered to an individual having a pattern B or pattern I predominant LDL particle size. In some embodiments, a compound of the present invention (e.g., the compound of Formula II) is administered to an individual having a predominant LDL particle size of less than 26.34 nm as measured by GGE, and optionally changing the predominant LDL particle size in the individual to a size greater than 26.34 nm as measured by GGE. In some embodiments, a compound of the present invention (e.g., the compound of Formula II) is administered to an individual having a predominant LDL particle size of less than 25.75 nm as measured by GGE, and optionally changing the predominant LDL particle size in the individual to a size greater than 25.75 nm, and optionally greater than 26.34 nm as measured by GGE.

In some embodiments, a compound of the present invention (e.g., the compound of Formula II) is administered to an individual having a predominant LDL particle size of less 212.0 nm as measured by AIM, and optionally changing the predominant LDL particle size in the individual to a size greater than 212.0 nm as measured by AIM. In some embodiments, a compound of the present invention (e.g., the compound of Formula II) is administered to an individual having a predominant LDL particle size of less 208.8 nm as measured by AIM, and optionally changing the predominant LDL particle size in the individual to a size greater than 208.8 nm, and optionally grater than 212.0 nm as measured by ATM.

In some embodiments, a compound of the present invention (e.g., the compound of Formula II) is administered to an individual having a predominant LDL-III particle as measured by AIM. In some embodiments, a compound of the present invention (e.g., the compound of Formula II) is administered to an individual having a predominant LDL-IV particle as measured by AIM.

In some embodiments, a compound of the present invention is administered to an individual having an Apolipoprotein B-100 level (e.g., blood level) of at least 130 mg/dl, e.g., at least 150 mg/dl, or 175 mg/dl, optionally also having an LDL particle size pattern B or I. In some embodiments, a compound of the present invention is administered to an individual having an Apolipoprotein B-100 level of at least 130 mg/dl in an amount and frequency sufficient to reduce the Apolipoprotein B-100 level, e.g., from above 130 mg/dl to below 130 mg/dl over a time period (e.g., 10, 20, 40, 70, 100 or more days) and/or to maintain a desired goal Apolipoprotein B-100 level, e.g., below 130 mg/dl, below 120 mg/dl, below 100 mg/dl, etc.

In some embodiments, a compound of the present invention is administered to an individual having a non-HDL cholesterol level (e.g., blood level) of at least 130 mg/dL, e.g., at least 150 mg/dL, optionally also having an LDL particle size pattern B or I. In some embodiments, a compound of the present invention is administered to an individual having a non-HDL cholesterol level of at least 130 mg/dL in an amount and frequency sufficient to reduce the non-HDL cholesterol level, e.g., from above 130 mg/dL to below 130 mg/dL, over a time period (e.g., 10, 20, 40, 70, 100 or more days) and/or to maintain a desired goal non-HDL cholesterol level, e.g., below 130 mg/dL.

In some embodiments, a compound of the present invention is administered to an individual having an LDL-cholesterol level (e.g., a fasting blood cholesterol level) of at least 130 mg/dL, e.g., at least 150 mg/dL, optionally also having an LDL particle size pattern B or I. In some embodiments, a compound of the present invention is administered to an individual having a cholesterol level of at least 130 mg/dL in an amount and frequency sufficient to reduce the cholesterol level, e.g., from above 130 mg/dL to below 110 mg/dL, over a time period (e.g., 10, 20, 40, 70, 100 or more days) and/or to maintain a desired goal cholesterol level, e.g., below 110 mg/dL.

In some embodiments, a compound of the present invention is administered to an individual having metabolic syndrome, optionally also having an LDL particle size pattern B or I. The metabolic syndrome is characterized by a group of metabolic risk factors in one person. They include: (a) abdominal obesity (excessive fat tissue in and around the abdomen); (b) atherogenic dyslipidemia (blood fat disorders—high triglycerides, low HDL cholesterol and high LDL cholesterol—that foster plaque buildups in artery walls); (c) elevated blood pressure; (d) insulin resistance or glucose intolerance (the body can't properly use insulin or blood sugar); (e) prothrombotic state (e.g., high fibrinogen or plasminogen activator inhibitor-1 in the blood); and (1) proinflammatory state (e.g., elevated C-reactive protein in the blood)

In some embodiments, a compound of the present invention is administered to an individual having diabetes or who is insulin resistant, optionally also having an LDL particle size pattern B or I, and/or a non-HDL cholesterol level greater or equal to 130 mg/dL.

In some embodiments, a compound of the present invention is administered to an individual having atherosclerosis, optionally also having an LDL particle size pattern B or I. In some embodiments, a compound of the present invention is administered to an individual not having atherosclerosis, but optionally having LDL particle size pattern B or I.

In some embodiments, an individual (e.g., a human) is tested for LDL particle size, Apolipoprotein B-100 level, LDL cholesterol level, triglyceride level, insulin resistance, and/or glucose tolerance prior to, during a course of treatment, and/or after administration of a compound of the present invention. Such tests are useful, e.g., for initially identifying individuals that will derive maximum benefit from the compounds, as well as for monitoring efficacy of the treatment and optionally, for determining treatment can be improved by a modified or alternate treatment. Thus, in some embodiments, the treatment of the individual is changed following the determination of LDL particle size, Apolipoprotein B-100 level, LDL cholesterol level, triglyceride level, insulin resistance, and/or glucose tolerance.

Measurement of blood levels of Apolipoprotein B-100, LDL cholesterol, triglyceride level, LDL particle size or other blood factors are generally determined from a blood sample from a fasting individual.

Two exemplary methods of determining LDL particle size include gradient-gel electrophoresis (GGE) and Airborne Ion Mobility (AIM) methods. While it is believed that the two methods produce substantially the same results, to the extent there is a difference in the two methods, AIM should be used to determine LDL particle size unless indicated otherwise. GGE is described in Krauss and Burke, *J Lipid Res.* 23:97-104 (1982) and La Belle, et al., *J. Lipid Res.* 38 690-700 (1997). AIM is described in Caulfield, et al., *Clin. Chem.* 54:1307-1316 (2008).

IV. Formulations and Administration

In accordance with the present invention, a therapeutically effective amount of a PPAR delta agonist (e.g., a compound of Formula I) can be used to, e.g., decrease the amount of small LDL particles, reduce Apolipoprotein B-100 blood levels, reduce LDL cholesterol blood levels, reduce triglyceride levels, raise HDL cholesterol levels, and/or reduce cholesterol synthesis and/or absorption as described herein.

The compositions of the invention can include compounds of Formula (I), pharmaceutically acceptable salts thereof or a hydrolysable precursor thereof. In some embodiments, the compound is mixed with suitable carriers or excipient(s) in a therapeutically effective amount.

The compounds of Formula (I) that are used in the methods of the present invention can be incorporated into a variety of formulations for therapeutic administration. More particularly, PPAR delta agonists, including the compounds of Formula (I), can be formulated into pharmaceutical compositions by combination with appropriate, pharmaceutically acceptable carriers or diluents and can be formulated into preparations in solid, semi-solid, liquid or gaseous forms, such as tablets, capsules, pills, powders, granules, dragees, gels, slurries, ointments, solutions, suppositories, injections, inhalants and aerosols. As such, administration of the compounds can be achieved in various ways, including oral, buccal, rectal, parenteral, intraperitoneal, intradermal, transdermal, intratracheal administration. Moreover, the compound can be administered in a depot or sustained release formulation. In addition, the compounds can be administered in a liposome.

The compounds of Formula (I) can be formulated with common excipients, diluents or carriers and compressed into tablets or formulated as elixirs or solutions for convenient oral administration or administered by the intramuscular or intravenous routes. The compounds can be administered transdermally and can be formulated as sustained release dosage forms and the like. Compounds of Formula (I) can be administered alone, in combination with each other or they can be used in combination with other known compounds.

Suitable formulations for use in the present invention are found in Remington's Pharmaceutical Sciences (Mack Publishing Company (1985) Philadelphia, Pa., 17th ed.), which is incorporated herein by reference. Moreover, for a brief review of methods for drug delivery, see, Langer, Science (1990) 249:1527-1533, which is incorporated herein by reference. The pharmaceutical compositions described herein can be manufactured in a manner that is known to those of skill in the art, i.e., by means of conventional mixing, dissolving, granulating, dragee-making, levigating, emulsifying, encapsulating, entrapping or lyophilizing processes. The following methods and excipients are merely exemplary and are in no way limiting.

For injection, the compounds can be formulated into preparations by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives. In some embodiments, the compounds of the present invention can be formulated in aqueous solutions, e.g., in physiologically compatible buffers such as Hanks's solution, Ringer's solution or physiological saline buffer. For transmucosal administration, penetrants appropriate to the barrier to be permeated are used in the formulation. Such penetrants are generally known in the art.

For oral administration, the compounds of Formula (I) can be formulated readily by combining with pharmaceutically acceptable carriers that are well known in the art. Such carriers enable the compounds to be formulated as tablets, pills, dragees, capsules, emulsions, lipophilic and hydrophilic suspensions, liquids, gels, syrups, slurries, suspensions and the like, for oral ingestion by a patient to be treated. Pharmaceutical preparations for oral use can be obtained by mixing the compounds with a solid excipient, optionally grinding a resulting mixture and processing the mixture of granules, after adding suitable auxiliaries, if desired, to obtain tablets or dragee cores. Suitable excipients are, in particular, fillers such as sugars, including lactose, sucrose, mannitol or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose and/or polyvinylpyrrolidone (PVP). If desired, disintegrating agents can be added, such as the cross-linked polyvinyl pyrrolidone, agar or alginic acid or a salt thereof such as sodium alginate.

Dragee cores are provided with suitable coatings. For this purpose, concentrated sugar solutions can be used, which can optionally contain gum arabic, talc, polyvinyl pyrrolidone, carbopol gel, polyethylene glycol and/or titanium dioxide, lacquer solutions and suitable organic solvents or solvent mixtures. Dyestuffs or pigments can be added to the tablets or dragee coatings for identification or to characterize different combinations of active compound doses.

Pharmaceutical preparations that can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches and/or lubricants such as talc or magnesium stearate and, optionally, stabilizers. In soft capsules, the active compounds can be dissolved or suspended in suitable liquids, such as fatty oils, liquid paraffin or liquid polyethylene glycols. In addition, stabilizers can be added. All formulations for oral administration should be in dosages suitable for such administration.

For buccal administration, the compositions can take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas or from propellant-free, dry-powder inhalers. In the case of a pressurized aerosol the dosage unit can be determined by providing a valve to deliver a metered amount. Capsules and cartridges of, e.g., gelatin for use in an inhaler or insufflator can be formulated containing a powder mix of the compound and a suitable powder base such as lactose or starch.

The compounds can be formulated for parenteral administration by injection, e.g., by bolus injection or continuous infusion. Formulations for injection can be presented in unit dosage form, e.g., in ampules or in multidose containers, with an added preservative. The compositions can take such forms as suspensions, solutions or emulsions in oily or aqueous vehicles and can contain formulator agents such as suspending, stabilizing and/or dispersing agents.

Pharmaceutical formulations for parenteral administration include aqueous solutions of the active compounds in water-soluble form. Additionally, suspensions of the active compounds can be prepared as appropriate oily injection suspensions. Suitable lipophilic solvents or vehicles include fatty oils such as sesame oil or synthetic fatty acid esters, such as ethyl oleate or triglycerides or liposomes. Aqueous injection suspensions can contain substances which increase the viscosity of the suspension, such as sodium carboxymethyl cellulose, sorbitol or dextran. Optionally, the suspension can also contain suitable stabilizers or agents which increase the solubility of the compounds to allow for the preparation of highly concentrated solutions. Alternatively, the active ingredient can be in powder form for constitution with a suitable vehicle, e.g., sterile pyrogen-free water, before use.

The compounds can also be formulated in rectal compositions such as suppositories or retention enemas, e.g., containing conventional suppository bases such as cocoa butter, carbowaxes, polyethylene glycols or other glycerides, all of which melt at body temperature, yet are solidified at room temperature.

In addition to the formulations described previously, the compounds can also be formulated as a depot preparation. Such long acting formulations can be administered by implantation (for example subcutaneously or intramuscularly) or by intramuscular injection. Thus, for example, the compounds can be formulated with suitable polymeric or hydrophobic materials (for example as an emulsion in an acceptable oil) or ion exchange resins or as sparingly soluble derivatives, for example, as a sparingly soluble salt.

Alternatively, other delivery types for hydrophobic pharmaceutical compounds can be employed. Liposomes and emulsions are well known examples of delivery vehicles or carriers for hydrophobic drugs. In a presently preferred embodiment, long-circulating, i.e., stealth liposomes can be employed. Such liposomes are generally described in Woodle, et al., U.S. Pat. No. 5,013,556. The compounds of the present invention can also be administered by controlled release means and/or delivery devices such as those described in U.S. Pat. Nos. 3,845,770; 3,916,899; 3,536,809; 3,598,123; and 4,008,719.

Certain organic solvents such as dimethylsulfoxide (DMSO) also can be employed, although usually at the cost of greater toxicity. Additionally, the compounds can be delivered using a sustained-release, such as semipermeable matrices of solid hydrophobic polymers containing the therapeutic agent. Various types of sustained-release materials have been established and are well known by those skilled in the art. Sustained-release capsules can, depending on their chemical nature, release the compounds for a few hours up to over 100 days.

The pharmaceutical compositions also can comprise suitable solid or gel phase carriers or excipients. Examples of such carriers or excipients include but are not limited to calcium carbonate, calcium phosphate, various sugars, starches, cellulose derivatives, gelatin and polymers such as polyethylene glycols.

Pharmaceutical compositions suitable for use in the present invention include compositions wherein the active ingredients are contained in a therapeutically effective amount. The amount of composition administered will, of course, be dependent on the subject being treated, on the subject's weight, the severity of the affliction, the manner of administration and the judgment of the prescribing physician. Determination of an effective amount is well within the capability of those skilled in the art, especially in light of the detailed disclosure provided herein.

For any compound used in the method of the present invention, a therapeutically effective dose can be estimated initially from cell culture assays or animal models.

Moreover, toxicity and therapeutic efficacy of the compounds described herein can be determined by standard pharmaceutical procedures in cell cultures or experimental animals, e.g., by determining the $LD_{50}$ (the dose lethal to 50% of the population) and the $ED_{50}$ (the dose therapeutically effective in 50% of the population). The dose ratio between toxic and therapeutic effect is the therapeutic index and can be expressed as the ratio between $LD_{50}$ and $ED_{50}$. Compounds that exhibit high therapeutic indices are generally preferred. The data obtained from these cell culture assays and animal studies can be used in formulating a dosage range that is not toxic for use in human. The dosage of such compounds lies preferably within a range of circulating concentrations that include the $ED_{50}$ with little or no toxicity. The dosage can vary within this range depending upon the dosage form employed and the route of administration utilized. The exact formulation, route of administration and dosage can be chosen by the individual physician in view of the patient's condition. (See, e.g., Fingl et al. 1975 In: The Pharmacological Basis of Therapeutics, Ch. 1).

The amount of active compound that can be combined with a carrier material to produce a single dosage form will vary depending upon the disease treated, the mammalian species and the particular mode of administration. Exemplary dosages will of course depend on the compound used. As a general guide, suitable unit doses for the compounds of the present invention can, for example, contain between 10 mg to about 3000 mg of the active compound, e.g., a unit dose between 50 mg to about 1500 mg, e.g. a unit dose between 50 to about 500 mg. As disclosed in the examples, 50, 100, and 200 mg doses of

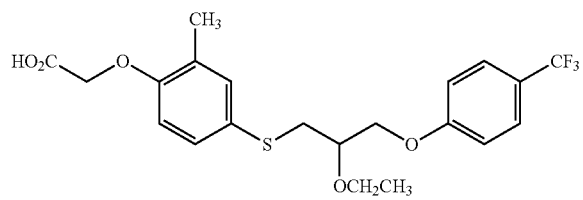 [SMILES: CCOC(COc1ccc(C(F)(F)F)cc1)CSc1ccc(OCC(=O)O)c(C)c1]

are effective in improving, e.g., LDL particle size in patients.

Unit doses (such as those discussed above) can be administered more than once a day, for example 2, 3, 4, 5 or 6 times a day, but optionally 1 or 2 times per day, so that the total daily dosage for a 70 kg adult is in the range of 0.1 to about 250 mg per kg weight of subject per administration. An exemplary dosage is 5 to about 250 mg per kg weight of subject per administration and such therapy can extend for a number of weeks or months and in some cases, years. It will be understood, however, that the specific dose level for any particular patient will depend on a variety of factors including the activity of the specific compound employed; the age, body weight, general health, sex and diet of the individual being treated; the time and route of administration; the rate of excretion; other drugs which have previously been administered; and the severity of the particular disease undergoing therapy, as is well understood by those of skill in the area.

A typical dosage can be one 10 to about 1500 mg tablet taken once a day or, multiple times per day or one time-release capsule or tablet taken once a day and containing a proportionally higher content of active ingredient. In some embodiments, a dosage of 10, 25, 50, 100, 200, or 300 mg a day is provided. The time-release effect can be obtained by capsule materials that dissolve at different pH values, by capsules that release slowly by osmotic pressure or by any other known means of controlled release.

It can be necessary to use dosages outside these ranges in some cases as will be apparent to those skilled in the art. Further, it is noted that the clinician or treating physician will know how and when to interrupt, adjust or terminate therapy in conjunction with individual patient response.

The compounds of the present invention may be used in combination with other pharmaceutically active agents.

Methods are known in the art for determining effective doses for therapeutic and prophylactic purposes for the disclosed pharmaceutical compositions or the disclosed drug combinations, whether or not formulated in the same composition. For therapeutic purposes, the term "jointly effective amount" as used herein, means that amount of each active compound or pharmaceutical agent, alone or in combination, that elicits the biological or medicinal response in a tissue system, animal or human that is being sought by a researcher, veterinarian, medical doctor or other clinician, which includes alleviation of the symptoms of the disease or disorder being treated. For prophylactic purposes (i.e., inhibiting the onset or progression of a disorder), the term "jointly effective amount" refers to that amount of each active compound or pharmaceutical agent, alone or in combination, that treats or inhibits in a subject the onset or progression of a disorder as being sought by a researcher, veterinarian, medical doctor or other clinician. Thus, the present invention provides combinations of two or more drugs wherein, for example, (a) each drug is administered in an independently therapeutically or prophylactically effective amount; (b) at least one drug in the combination is administered in an amount that is sub-therapeutic or sub-prophylactic if administered alone, but is therapeutic or prophylactic when administered in combination with the second or additional drugs according to the invention; or (c) both (or more) drugs are administered in an amount that is sub-therapeutic or sub-prophylactic if administered alone, but are therapeutic or prophylactic when administered together.

Anti-diabetic agents include thiazolidinedione and non-thiazolidinedione insulin sensitizers, which decrease peripheral insulin resistance by enhancing the effects of insulin at target organs and tissues, as well as sulfonylureas (e.g., glyburide), biguanides (e.g. metformin), DPP-4 inhibitors (e.g., sitagliptin), incretin analogs (e.g., exenatide), meglitinides (e.g., Nateglinide), and α-glucosidase inhibitors (e.g., acarbose).

Some of the following agents are known to bind and activate the nuclear receptor peroxisome proliferator-activated receptor-gamma (PPARγ) which increases transcription of specific insulin-responsive genes. Examples of PPAR-gamma agonists are thiazolidinediones such as: (1) rosiglitazone (2,4-thiazolidinedione, 5-((4-(2-(methyl-2-pyridinylamino)ethoxy)phenyl)methyl)-, (Z)-2-butenedioate (1:1) or 5-((4-(2-(methyl-2-pyridinylamino)ethoxy)phenyl)methyl)-2,4-thiazolidinedione, known as AVANDIA™; also known as BRL 49653, BRL 49653C, BRL 49653c, SB 210232, or rosiglitazone maleate); (2) pioglitazone (2,4-thiazolidinedione, 5-((4-(2-(5-ethyl-2-pyridinyl) ethoxy) phenyl)methyl)-, monohydrochloride, (+−)- or 5-((4-(2-(5-ethyl-2-pyridyl)ethoxy)phenyl)methyl)-2,4-thiazolidinedione, known as ACTOS™, ZACTOS™, or GLUSTIN™; also known as AD 4833, U 72107, U 72107A, U 72107E, pioglitazone hydrochloride (USAN™)); (3) troglitazone (5-((4-((3,4-dihydro-6-hydroxy-2,5,7,8-tetramethyl-2H-1-benzopyran-2-yl)methoxy)phenyl)methyl)-2,4-thiazolidinedione, known as NOSCAL™, REZULIN™, ROMOZIN™, or PRELAY™; also known as Cl 991, CS 045, GR 92132, GR 92132x); (4) isaglitazone ((+)-5-[[6-[(2-fluorophenyl)methoxy]-2-naphthalenyl]methyl]-2,4-thiazolidinedione or 5-((6-((2-fluorophenyl)methoxy)-2-naphthalenyl) methyl-2,4-thiazolidinedione or 5-(6-(2-fluorobenzyloxy)naphthalen-2-ylmethyl)thiazolidine-2,4-dione, also known as MCC-555 or neoglitazone); and (5) 5-BTZD.

Additionally, the non-thiazolidinediones that act as insulin sensitizing agents include, but are not limited to: (1) JT-501 (JTT 501, PNU-1827, PNU-716-MET-0096, or PNU 182716: isoxazolidine-3,5-dione, 4-((4-(2-phenyl-5-methyl)-1,3-oxazolyl) ethylphenyl-4) methyl-); (2) KRP-297 (5-(2,4-dioxothiazolidin-5-ylmethyl)-2-methoxy-N-(4-trifluoromethyl)benzyl)benzamide or 5-((2,4-dioxo-5-thiazolidinyl), methyl)-2-methoxy-N-((4-(trifluoromethyl) phenyl)methyl) benzamide); and (3) Farglitazar (L-tyrosine, N-(2-benzoylphenyl)-O-(2-(2-phenyl-4-oxazolyl) ethyl)- or N-(2-benzoylphenyl)-O-(2-(5-methyl-2-phenyl-4-oxazolyl)ethyl)-L-tyrosine, or GW2570 or GI-262570).

Other agents have also been shown to have PPAR modulator activity such as PPAR gamma, SPPAR gamma, and/or PPAR delta/gamma agonist activity. Examples are listed below: (1) AD 5075; (2) R 119702 ((+−)-5-(4-(5-Methoxy-1H-benzimidazol-2-ylmethoxy) benzyl)thiazolin-2,4-dione hydrochloride, or Cl 1037 or CS 011); (3) CLX-0940 (peroxisome proliferator-activated receptor alpha agonist/peroxisome proliferator-activated receptor gamma agonist); (4) LR-90 (2,5,5-tris(4-chlorophenyl)-1,3-dioxane-2-carboxylic acid, PPARdelta/γ agonist); (5) Tularik (PPARγ agonist); (6) CLX-0921 (PPARγ agonist); (7) CGP-52608 (PPAR agonist); (8) GW-409890 (PPAR agonist); (9) GW-7845 (PPAR agonist); (10) L-764406 (PPAR agonist); (11) LG-101280 (PPAR agonist); (12) LM-4156 (PPAR agonist); (13) Risarestat (CT-112); (14) YM 440 (PPAR agonist); (15) AR-H049020 (PPAR agonist); (16) GW 0072 (4-(4-((2S,5S)-5-(2-(bis(phenylmethyl)amino)-2-oxoethyl)-2-heptyl-4-oxo-3-thiazolidinyl)butyl)benzoic acid); (17) GW 409544 (GW-544 or GW-409544); (18) NN 2344 (DRF 2593); (19) NN 622 (DRF 2725); (20) AR-H039242 (AZ-242); (21) GW 9820 (fibrate); (22) GW 1929 (N-(2-benzoylphenyl)-O-(2-(methyl-2-pyridinylamino) ethyl)-L-tyrosine, known as GW 2331, PPAR α/γ agonist); (23) SB 219994 ((S)-4-(2-(2-benzoxazolylmethylamino)ethoxy)-alpha-(2,2,2-trifluor-oethoxy)benzenepropanoic acid or 3-(4-(2-(N-(2-benzoxazolyl)-N-methylamino)ethoxy)phenyl)-2 (S)-(2, 2, 2-trifluoroethoxy)propionic acid or benzenepropanoic acid, 4-(2-(2-benzoxazolylmethylamino)ethoxy)-alpha-(2,2,2-trifluoroethoxy)-, (alphaS)-, PPAR α/γ agonist); (24) L-796449 (PPAR α/γ agonist); (25) Fenofibrate (Propanoic acid, 2-[4-(4-chlorobenzoyl)phenoxy]-2-methyl-, 1-methylethyl ester, known as TRICOR™, LIPCOR™, LIPANTIL™, LIPIDIL™ MICRO PPAR alpha agonist); (26) GW-9578 (PPAR alpha agonist); (27) GW-2433 (PPAR alpha/γ agonist); (28) GW-0207 (PPAR γ agonist); (29) LG-(PPAR γ agonist); (30) LY-300512 (PPAR γ agonist); (31) NID525-209 (NID-525); (32) VDO-52 (VDO-52); (33) LG 100754 (peroxisome proliferator-activated receptor agonist); (34) LY-510929 (peroxisome proliferator-activated receptor agonist); (35) bexarotene (4-(1-(3,5,5,8,8-pentamethyl-5,6,7,8-tetrahydro-2-naphthalenyl)ethenyl)benzoic acid, known as TARGRETIN™, TARGRETYN™, TARGREXIN™; also known as LGD 1069, LG 100069, LG 1069, LDG 1069, LG 69, RO 264455); and (36) GW-1536 (PPAR alpha/γ agonist).

In some embodiments a PPAR delta agonist of the present invention is combined with a compound of one of the following formulae:

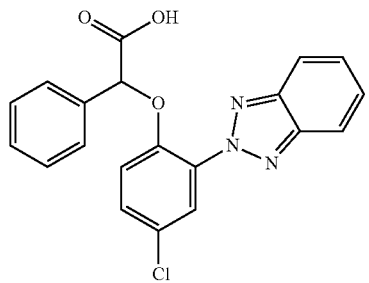

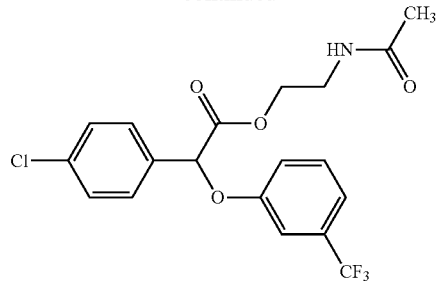

or a pharmaceutically acceptable salt or solvate thereof. The compound according to the above right formula can be the racemate, (+) isomer or the (−) isomer. Methods for making such compounds are taught in U.S. Patent Application Publication No. 20030220399 which is incorporated herein by reference. Methods of resolving alpha-(phenoxy)phenylacetic acid derivatives are taught in U.S. Patent Application Publication No. 20050033084 which is incorporated herein by reference in its entirety.

(B) Other insulin sensitizing agents include, but are not limited to: (1) INS-1 (D-chiroinositol or D-1, 2, 3, 4, 5, 6-hexahydroxycyclohexane); (2) protein tyrosine phosphatase 1B (PTP-1B) inhibitors; (3) glycogen synthase kinase-3 (GSK3) inhibitors; (4) beta 3 adrenoceptor agonists such as ZD 2079 ((R)—N-(2-(4-(carboxymethyl)phenoxy) ethyl)-N-(2-hydroxy-2-phenethyl) ammonium chloride, also known as ICI D 2079) or AZ 40140; (5) glycogen phosphorylase inhibitors; (6) fructose-1,6-bisphosphatase inhibitors; (7) chromic picolinate, vanadyl sulfate (vanadium oxysulfate); (8) KP 102 (organo-vanadium compound); (9) chromic polynicotinate; (10) potassium channel agonist NN 414; (11) YM 268 (5,5'-methylene-bis(1,4-phenylene)bismethylenebis(thiazolidine-2,4-dione); (12) TS 971; (13) T 174 ((+−)-5-(2,4-dioxothiazolidin-5-ylmethyl)-2-(2-naphthylmethyl)benzoxazole-); (14) SDZ PGU 693 ((+)-trans-2 (S-((4-chlorophenoxy)methyl)-7alpha-(3,4-dichlorophenyl)tetrahydropyrrolo (2,1-b)oxazol-5 (6H)-one); (15) S 15261 ((−)-4-(2-((9H-fluoren-9-ylacetyl)amino)ethyl)benzoic acid 2-((2-methoxy-2-(3-(trifluoromethyl)phenyl)ethyl)amino) ethyl ester); (16) AZM 134 (Alizyme); (17) ARIAD; (18) R 102380; (19) PNU 140975 (1-(hydrazinoiminomethyl)hydrazino)acetic acid; (20) PNU 106817 (2-(hydrazinoiminomethyl)hydrazino)acetic acid; (21) NC 2100 (5-((7-(phenylmethoxy)-3-quinolinyl)methyl)-2,4-thiazolidinedione; (22) MXC 3255; (23) MBX 102; (24) ALT 4037; (25) AM 454; (26) JTP 20993 (2-(4-(2-(5-methyl-2-phenyl-4-oxazolyl)ethoxy) benzyl)-malonic acid dimethyl diester); (27) Dexlipotam (5 (R)-(1,2-dithiolan-3-yl)pentanoic acid, also known as (R)-alpha lipoic acid or (R)-thioctic acid); (28) BM 170744 (2,2-Dichloro-12-(p-chlorophenyl)dodecanoic acid); (29) BM 152054 (5-(4-(2-(5-methyl-2-(2-thienyl)oxazol-4-yl)ethoxy) benzothien-7-ylmethyl)thiazolidine-2,4-dione); (30) BM 131258 (5-(4-(2-(5-methyl-2-phenyloxazol-4-yl)ethoxy) benzothien-7-ylmethyl)thiazolidine-2,4-dione); (31) CRE 16336 (EML 16336); (32) HQL 975 (3-(4-(2-(5-methyl-2-phenyloxazol-4-yl)ethoxy)phenyl)-2 (S)-(propylamino)propionic acid); (33) DRF 2189 (5-((4-(2-(1-Indolyl)ethoxy)phenyl) methyl)thiazolidine-2, 4-dione); (34) DRF 554158; (35) DRF-NPCC; (36) CLX 0100, CLX 0101, CLX 0900, or CLX 0901; (37) IkappaB Kinase (IKK B) Inhibitors (38) mitogen-activated protein kinase (MAPK) inhibitors p38 MAPK Stimulators (39) phosphatidyl-inositide triphosphate (40) insulin recycling receptor inhibitors

(41) glucose transporter 4 modulators (42) TNF-α antagonists (43) plasma cell differentiation antigen-1 (PC-1) Antagonists (44) adipocyte lipid-binding protein (ALBP/aP2) inhibitors (45) phosphoglycans (46) Galparan; (47) Receptron; (48) islet cell maturation factor, (49) insulin potentiating factor (IPF or insulin potentiating factor-1); (50) somatomedin C coupled with binding protein (also known as IGF-BP3, IGF-BP3, SomatoKine); (51) Diab II (known as V-411) or Glucanin, produced by Biotech Holdings Ltd. or Volque Pharmaceutical; (52) glucose-6 phosphatase inhibitors; (53) fatty acid glucose transport protein; (54) glucocorticoid receptor antagonists; and (55) glutamine:fructose-6-phosphate amidotransferase (GFAT) modulators.

(C) Biguanides, which decrease liver glucose production and increases the uptake of glucose. Examples include metformin such as: (1) 1,1-dimethylbiguanide (e.g., Metformin-DepoMed, Metformin-Biovail Corporation, or METFORMIN™ GR (metformnin gastric retention polymer)); and (2) metformin hydrochloride (N,N-dimethylimidodicarbonimidic diamide monohydrochloride, also known as LA 6023, BMS 207150, GLUCOPHAGE™, or GLUCOPHAGE XR™.

(D) Alpha-glucosidase inhibitors, which inhibit alpha-glucosidase. Alpha-glucosidase converts fructose to glucose, thereby delaying the digestion of carbohydrates. The undigested carbohydrates are subsequently broken down in the gut, reducing the post-prandial glucose peak. Examples include, but are not limited to: (1) acarbose (D-glucose, O-4,6-dideoxy-4-(((1 S-(1alpha,4alpha,5beta,6alpha))-4,5, 6-trihydroxy-3-(hydroxymethyl)-2-cyclohexen-1-yl) amino)-alpha-D-glucopyranosyl-(1-4)-O-alpha-D-glucopyranosyl-(1-4)-, also known as AG-5421, Bay-g-542, BAY-g-542, GLUCOBAY™, PRECOSE™, GLUCOR™, PRANDASE™, GLUMIDA™, or ASCAROSE™); (2) Miglitol (3,4,5-piperidinetriol, 1-(2-hydroxyethyl)-2-(hydroxymethyl)-, (2R (2alpha, 3beta, 4alpha, 5beta))- or (2R, 3R,4R,5S)-1-(2-hydroxyethyl)-2-(hydroxymethyl-3,4,5-piperidinetriol, also known as BAY 1099, BAY M 1099, BAY-m-1099, BAYGLITOL™, DIASTABOL™, GLYSET™, MIGLIBAY™, MITOLBAY™, PLUMAROL™); (3) CKD-711 (0-4-deoxy-4-((2,3-epoxy-3-hydroxymethyl-4,5,6-trihydroxycyclohexane-1-yl-)amino)-alpha-b-glucopyranosyl-(1-4)-alpha-D-glucopyranosyl (1-4)-D-glucopyranose); (4) emiglitate (4-(2-((2R,3R,4R,5S)-3,4,5-trihydroxy-2-(hydroxymethyl)-1-piperidinyl)ethoxy) benzoic acid ethyl ester, also known as BAY o 1248 or MKC 542); (5) MOR 14 (3,4,5-piperidinetriol, 2-(hydroxymethyl)-1-methyl-, (2R-(2alpha,3beta,4alpha,5beta))-, also known as N-methyldeoxynojirimycin or N-methylmoranoline); and (6) Voglibose (3,4-dideoxy-4-((2-hydroxy-1-(hydroxymethyl)ethyl)amino)-2-C-(hydroxymethyl)-D-epi-inositol or D-epi-Inositol,3,4-dideoxy-4-((2-hydroxy-1-(hydroxymethyl)ethyl)amino)-2-C-(hydroxymethyl)-, also known as A 71100, AO 128, BASEN™, GLUSTAT™, VOGLISTAT™.

(E) Insulins include regular or short-acting, intermediate-acting, and long-acting insulins, non-injectable or inhaled insulin, tissue selective insulin, glucophosphokinin (D-chiroinositol), insulin analogues such as insulin molecules with minor differences in the natural amino acid sequence and small molecule mimics of insulin (insulin mimetics), and endosome modulators. Examples include, but are not limited to: (1) Biota; (2) LP 100; (3) (SP-5-21)-oxobis(1-pyrrolidinecarbodithioato-S,S) vanadium, (4) insulin aspart (human insulin (28B-L-aspartic acid) or B28-Asp-insulin, also known as insulin X14, INA-X14, NOVORAPID™, NOVO-MIX™, or NOVOLOG™); (5) insulin detemir (Human 29B-(N-6-(1-oxotetradecyl)-L-lysine)-(1A-21A), (1B-29B)-Insulin or NN 304); (6) insulin lispro ("28B-L-lysine-29B-L-proline human insulin," or Lys(B28), Pro(B29) human insulin analog, also known as lys-pro insulin, LY 275585, HUMALOG™, HUMALOG™ MIX 75/25, or HUMALOG™ MIX 50/50); (7) insulin glargine (human (A21-glycine, B31-arginine, B32-arginine) insulin HOE 901, also known as LANTUS™, OPTISULIN™); (8) Insulin Zinc Suspension, extended (Ultralente), also known as HUMULIN™ U or ULTRALENTE™; (9) Insulin Zinc suspension (Lente), a 70% crystalline and 30% amorphous insulin suspension, also known as LENTE ILETIN™ II, HUMULIN™ L, or NOVOLIN™ L; (10) HUMULIN™ 50/50 (50% isophane insulin and 50% insulin injection); (11) HUMULIN™ 70/30 (70% isophane insulin NPH and 30% insulin injection), also known as NOVOLIN™70/30, NOVOLIN™ 70/30 PenFill, NOVOLIN™ 70/30 Prefilled; (12) insulin isophane suspension such as NPHILETIN™ II, NOVOLIN™ N, NOVOLIN™ N PenFill, NOVOLIN™ N Prefilled, HUMULIN™ N; (13) regular insulin injection such as ILETIN™ II Regular, NOVOLIN™ R, VELOSULIN™ BR, NOVOLIN™ R PenFill, NOVOLIN™ R Prefilled, HUMULIN™ R, or Regular U-500 (Concentrated); (14) ARIAD™; (15) LY 197535; (16) L-783281; and (17) TE-17411.

(F) Insulin secretion modulators such as: (1) glucagon-like peptide-1 (GLP-1) and its mimetics; (2) glucose-insulinotropic peptide (GIP) and its mimetics; (3) exendin and its mimetics; (4) dipeptyl protease (DPP or DPPIV) inhibitors such as (4a) DPP-728 or LAF 237 (2-pyrrolidinecarbonitrile, 1-(((2-((5-cyano-2-pyridinyl)amino)ethyl)amino) acetyl), known as NVP-DPP-728, DPP-728A, LAF-237); (4b) P 3298 or P32/98 (di-(3N-((2S, 3S)-2-amino-3-methyl-pentanoyl)-1,3-thiazolidine)fumarate); (4c) TSL 225 (tryptophyl-1,2,3,4-tetrahydroisoquinoline-3-carboxylic acid); (4d) Valine pyrrolidide (valpyr); (4e) 1-aminoalkylisoquinolinone-4-carboxylates and analogues thereof; (4f), SDZ, 272 070 (1-(L-Valyl)pyrrolidine); (4g) TMC-2A, TMC-2B, or TMC-2C; (4h) Dipeptide nitriles (2-cyanopyrrolodides); (4i) CD26 inhibitors; and (4j) SDZ 274-444; (5) glucagon antagonists such as AY-279955; and (6) amylin agonists which include, but are not limited to, pramlintide (AC-137, Symlin, tripro-amylin or pramlintide acetate).

The present compounds may increase insulin sensitivity with little or no increase in body weight than that found with the use of existing PPAR gamma agonists. Oral anti-diabetic agents may include insulin, sulfonylureas, biguanides, meglitinides, AGI's, PPAR alpha agonists, and PPAR gamma agonists, and dual PPAR alpha/gamma agonists.

The present compounds also may increase fat and/or lipid metabolism, providing a method for losing weight, losing fat weight, lowering body mass index, lowering lipids (such as lowering triglycerides), or treating obesity or the condition of being overweight. Examples of lipid lowering agents include bile acid sequestrants, fibric acid derivatives, nicotinic acid, and HMGCoA reductase inhibitors. Specific examples include statins such as LIPITOR™, ZOCOR™, PRAVACHOL™, LESCOL™, and MEVACOR™, and pitavastatin (nisvastatin) (Nissan, Kowa Kogyo, Sankyo, Novartis) and extended release forms thereof, such as ADX-159 (extended release lovastatin), as well as Colestid, Locholest, Questran, Atromid, Lopid, and Tricor.

Examples of blood pressure lowering agents include anti-hypertensive agents, such as angiotensin-converting enzyme (ACE) inhibitors (Accupril, Altace, Captopril, Lotensin, Mavik, Monopril, Prinivil, Univasc, Vasotec, and Zestril), adrenergic blockers (such as Cardura, Dibenzyline, Hylorel, Hytrin, Minipress, and Minizide) alpha/beta adrenergic blockers (such as Coreg, Normodyne, and Trandate), calcium channel blockers (such as Adalat, Calan, Cardene, Cardizem, Covera-HS, Dilacor, DynaCirc, Isoptin, Nimotop, Norvace, Plendil, Procardia, Procardia XL, Sula, Tiazac, Vascor, and Verelan), diuretics, angiotensin 11 receptor antagonists (such as Atacand, Avapro, Cozaar, and Diovan), beta adrenergic blockers (such as Betapace, Blocadren, Brevibloc, Cartrol, Inderal, Kerlone, Lavatol, Lopressor, Sectral, Tenormin, Toprol-XL, and Zebeta), vasodilators (such as Deponit, Dilatrate, SR, Imdur, Ismo, Isordil, Isordil Titradose, Monoket, Nitro-Bid, Nitro-Dur, Nitrolingual Spray, Nitrostat, and Sorbitrate), and combinations thereof (such as Lexxel, Lotrel, Tarka, Teczem, Lotensin HCT, Prinzide, Uniretic, Vaseretic, Zestoretic).

In some embodiments, the methods of the invention comprise chronic administration of a compound of the invention.

EXAMPLES

Example 1: Compound II Affects Concentrations of LDL Particle Subclasses

Elevated plasma concentrations of low-density lipoprotein (LDL) increase the risk for cardiovascular disease. Further, lipoprotein profiles relatively rich in small, dense LDL particles (subclass pattern B) as determined by Airborne Ion Mobility, are associated with greater risk than those that mainly consist of large, buoyant LDL particles (subclass pattern A). We have demonstrated that the compound of Formula II, a PPAR delta activator, effectively increased the predominant LDL particle size, in part by decreasing the amount of smaller LDL particles.

Thirty-six healthy male subjects were treated with the compound of Formula II at 50, 100, and 200 mg for 21 days. To determine the lipoprotein particle sizes in the subjects before and after administration of the compound, gradient-gel electrophoresis (GGE) and Airborne Ion Mobility (AIM) methods were used.

GGE was performed essentially as described in Krauss and Burke, *J Lipid Res.* 23:97-104 (1982) and La Belle, et al., *J. Lipid Res.* 38 690-700 (1997) as follows:

LDL particle diameters were determined by nondenaturing 2-14% polyacrylamide gradient gel electrophoresis in 0.09 M Tris/0.08 M borate buffer (pH 8.3), 3 mM EDTA at 8-10° C. Samples (whole plasma) were electrophoresed at 40 V for 15 min, then 80 V for 15 min, and then at 125 V for 24 h to allow all particles to run to their size exclusion limits. Gels were stained for protein with Sudan Black and scanned at 555 nm with a Transidyne RFT densitometer. Particle sizes were calculated from a calibration curve using a high molecular weight reference protyin mixture (Pharmacia Biotech., Piscataway, N.J.), 380 Å latex beads (Duke Scientific Corp., Palo Alto, Calif.) and lipoprotein calibrators that are frozen at −80° C. and included on each gel run. Plasma samples, stored at −80° C. and used as controls for gradient gel analysis procedures, were run in duplicate on each gel. Particle size of LDL peaks in the controls were measured within ±2 Å (coefficient of variation, +1%).

AIM was performed essentially as described in Caulfield, et al., *Clin. Chem.* 54:1307-1316 (2008), generally as follows:

Sample Preparation:

Serum samples or controls were briefly mixed by vortex mixing, then 5 µl of sample or control was mixed with 20 µl of an albumin removal reagent [7.5 g/L Reactive green 19 dextran (RGD), Sigma-Aldrich; 2.5 g/L dextran sulfate, Sigma-Aldrich; and 0.5 g/L EDTA, Spectrum Chemicals] and incubated on ice for 15 minutes. After incubation, the sample mixture was overlaid on 200 µl deuterium oxide (Medical Isotopes) in a 42.2 ultracentrifuge tube (Beckman Coulter). The samples were ultracentrifuged at 10° C. for 135 min at 223 000 g (42 000 rpm), and then the top 85 µl (i.e., the lipid fraction) of the sample was removed. The samples were diluted 1:800 for HDL analysis using 25 mmol/L ammonium acetate, 0.5 mmol/L ammonium hydroxide, pH 7.4. For LDL analysis, samples were diluted 1:200 with the same diluent containing 5 µg/mL dextran sulfate to help prevent LDL particles from sticking to the capillary surfaces. Final dilutions were made in deep-well 96-well plates and placed in a Leap HTLC Pal autosampler (Eksigent) with the cooled stack maintained at 6° C.

Lipoprotein Analysis:

The autosampler was connected to the electrospray generator (Model 3480; TSI) via methyl-deactivated silica capillary (50 µm i.d.; SGE). Flow was introduced by nano-LC pumps (Eksigent) running a mobile phase of 25 mmol/L ammonium acetate, 0.5 mmol/L ammonium hydroxide, pH 7.4. By means of a capillary metal union (Upchurch Scientific), an autosampler injected 10 µl sample at 6 µl/min into a transfer capillary (methyl-deactivated, SGE, 50 µm, 33 cm long). High voltage (2.1 kV) was applied to the metal capillary union located 33 cm upstream of the electrospray unit. The electrospray Taylor cone was monitored visually and amperometrically to ensure stability. After the sample had filled the capillary and reached the electrospray chamber, the flow was decreased to 200 nL/min and the data recording process was started. The gas (containing approximately 5% $CO_2$) flowing into the electrospray chamber was regulated at 1.6 L/min. The electrosprayed particles passed through a particle-charge neutralizing chamber and then entered the differential mobility analyzer (DMA). Se, e.g., U.S. Pat. No. 7,259,018. Scan time was 2 min and covered a particle range of 17.2 to 542.0 Å. After a scan was completed, data for specific ranges of particles corresponding to lipoprotein subclasses were pooled by totaling the particles across a predetermined set of 0.1-s bins that corresponded to particular subclasses, and the predominant LDL particle size (modal diameter) was determined.

Results

Lipid analysis of phase I multiple ascending doses (MAD) samples indicated that MBX-8025 significantly lowered LDL-cholesterol and Apolipoprotein B (FIG. 1).

To further understand the mechanism of action of the compound of Formula II ("Compound II"), plasma samples from pre-treatment (day 1) and post-treatment (day 21) were analyzed to determine LDL particle size by gradient-gel electrophoresis. LDL subclass pattern A, B, or I was assigned to each subject samples according to LDL particle peak diameter size (Pattern A: >263.4 A, Pattern I: 257.5-263.4 A, Pattern B: <257.5 A).

Figure 2:
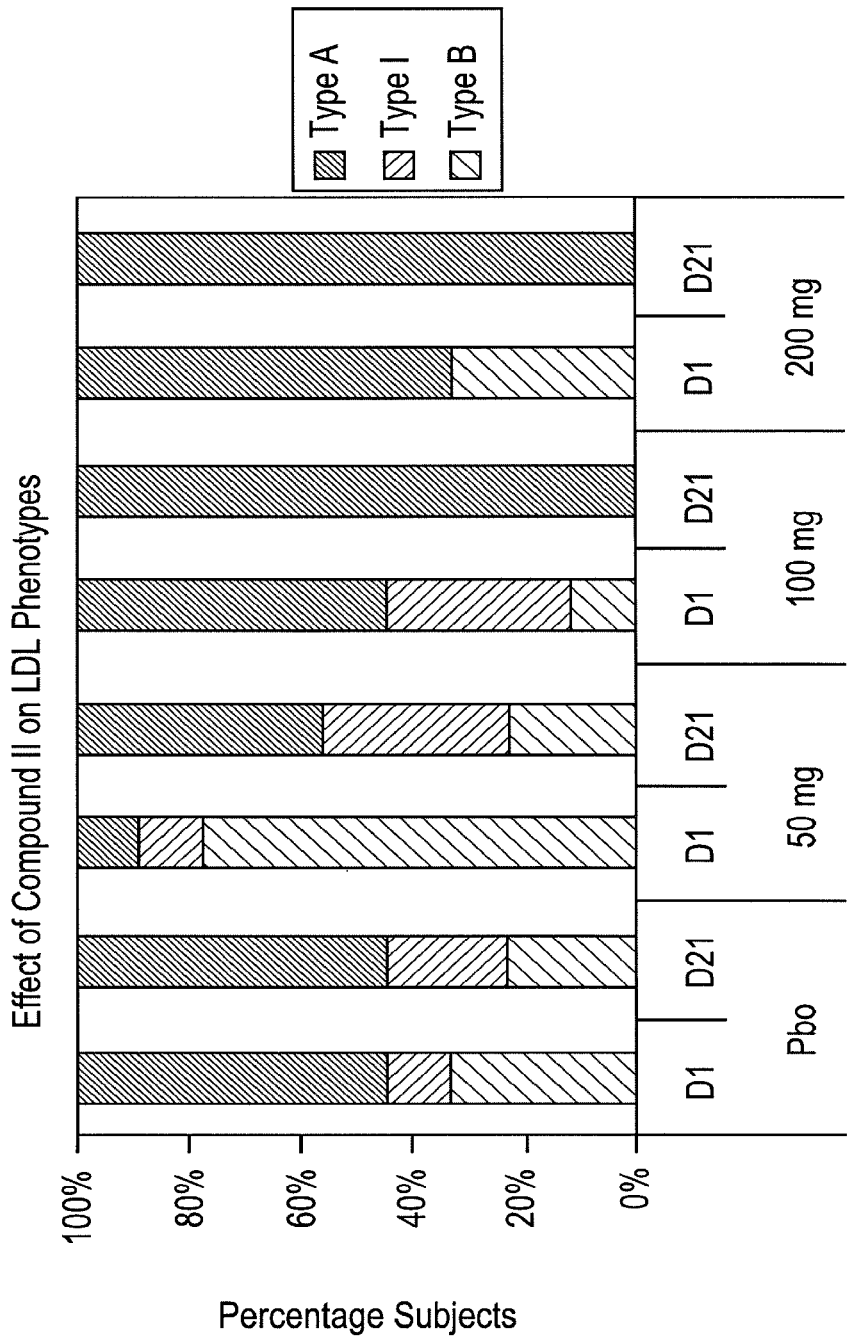
FIG. 2 illustrates the effect of Compound II on LDL pattern after 21 days of treatment.
Figure 3:
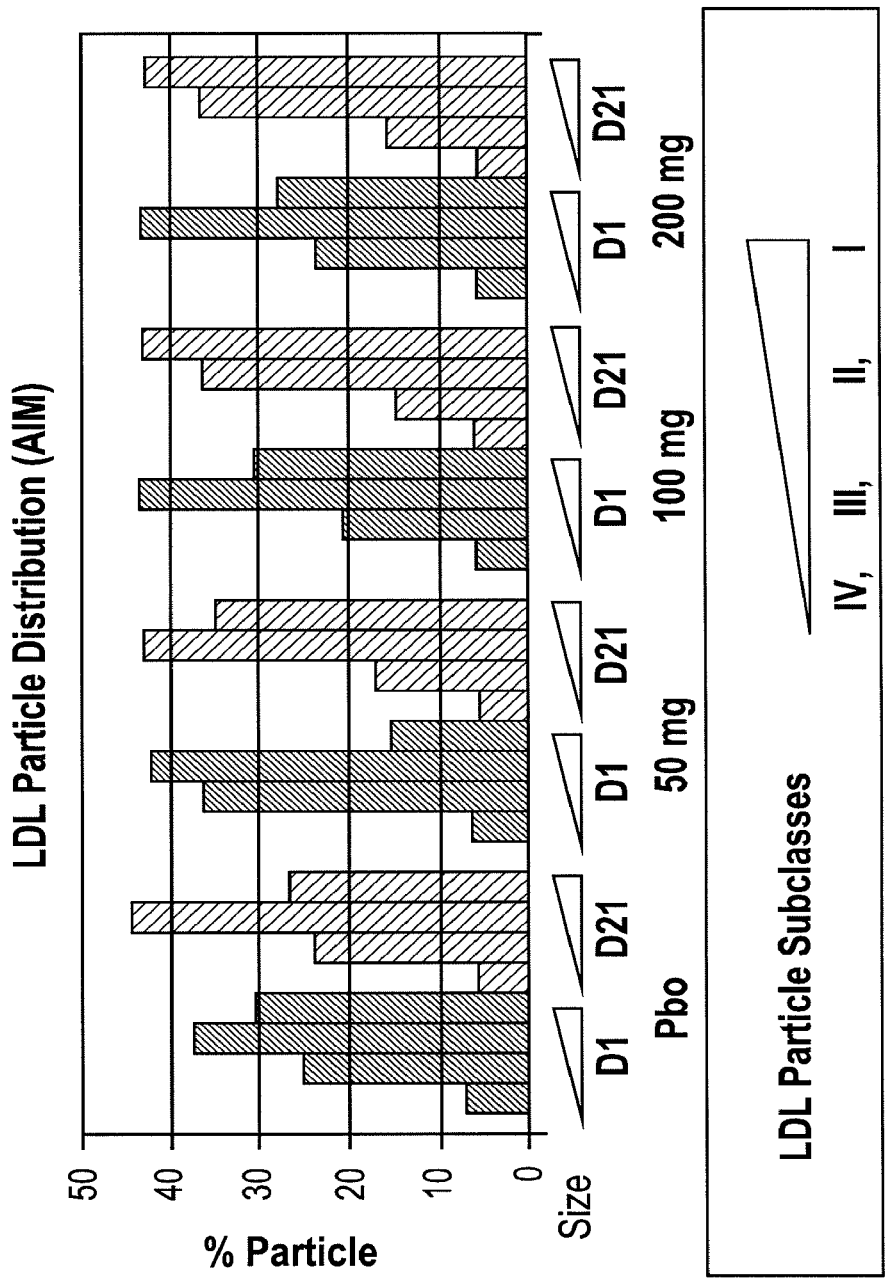
FIG. 3 illustrates changes in LDL particle distribution as a function of dosage of Compound II (determined by AIM).
Figure 4:
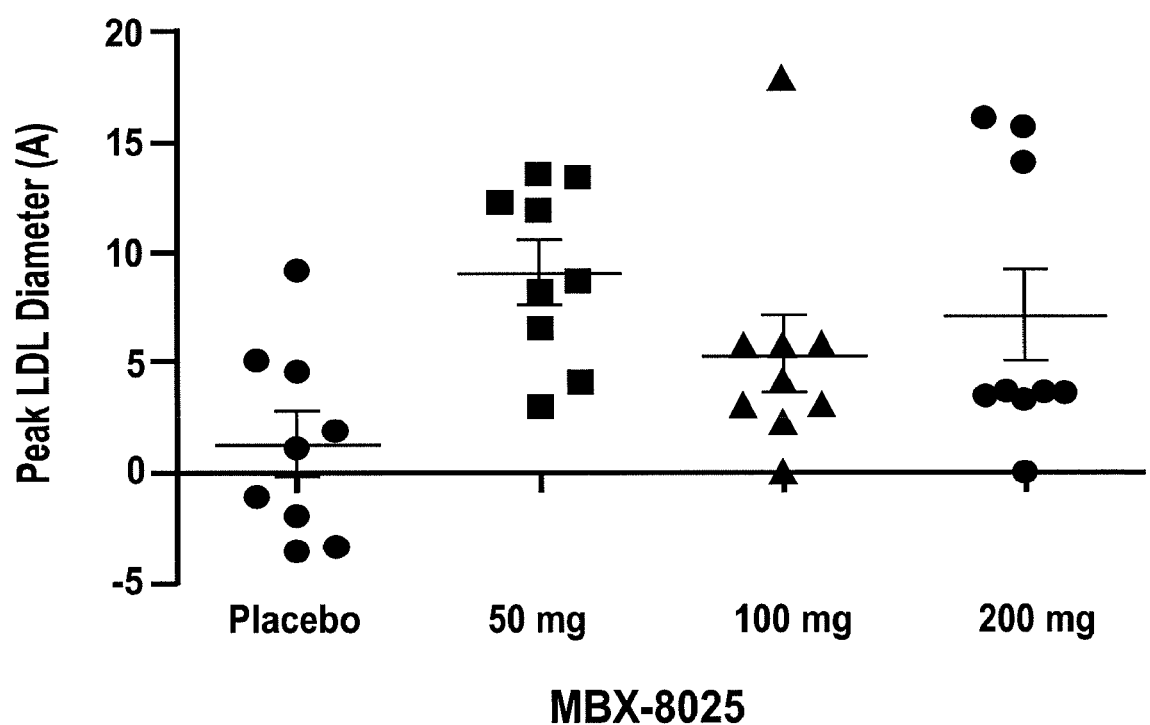
FIG. 4 illustrates the effect of Compound II on peak LDL diameter after 21 days of treatment.
Figure 5:
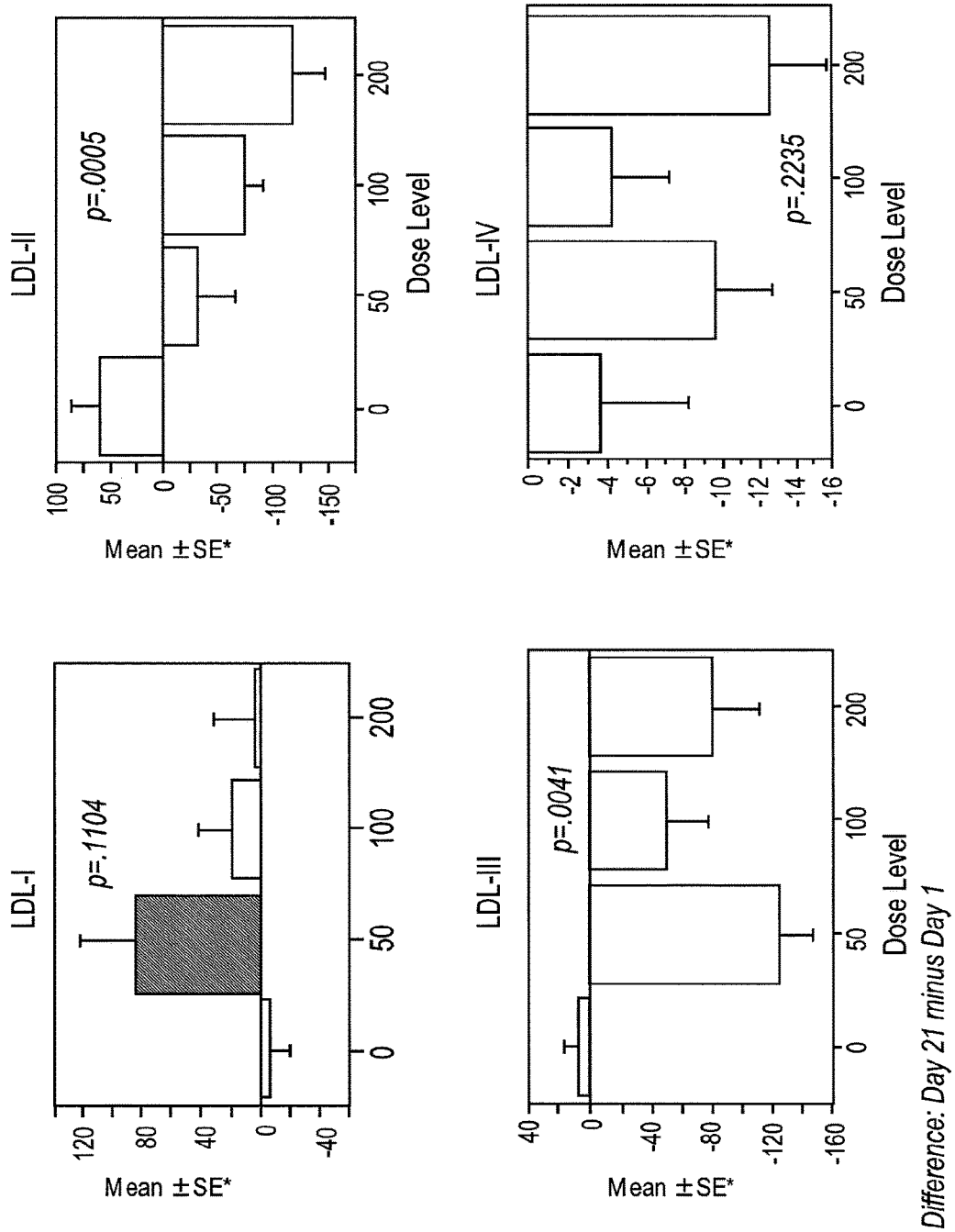
FIG. 5 illustrates the effect of Compound II after 21 days on LDL particle subclasses.

An inverse relationship between plasma triglyceride concentration and peak (i.e., predominant) LDL diameter in day 21 samples was observed. As shown in FIGS. 2, 3, and 4, compound II treatment increased the predominant LDL particle size, lowered the proportion of small LDL particles and therefore shifted the predominant LDL particle size from LDL Pattern B or I to LDL Pattern A at the 50, 100, and 200 mg dosage. Compound II did not affect VLDL particle size but did affect LDL particle distributions in dose dependent fashion. FIG. 5 illustrates the effect of Compound II after 21 days on LDL particle subclasses.

A second clinical study to determine the effect of the Compound of Formula II on LDL particle size in overweight subjects was performed. Subjects in this study met the following criteria: Non-Diabetic; untreated or diet-treated, with fasting lipids at initial screening and visit 2 (after 4 week run-in): TGs≥150 but ≤550 mg/dL; LDL≥130 but ≤280 mg/dL; HDL≥60 mg/dL. Subjects were males with waist circumference greater than 38" or females with waist circumference greater than 33". Data was generated in this second study from 181 subjects.

Table I shows the number of subjects having the indicated LDL pattern before or after the indicated time period following the beginning of treatment. For example, in the placebo group, at the beginning of the study, 10 subjects had LDL pattern A, 3 subjects had LDL pattern I and 16 subjects had LDL pattern B. After 8 weeks on placebo, there were only 6 subjects with LDL pattern A and 13 subjects with LDL pattern B. Of the 28 subjects that remained in the study in the placebo group, there was a net loss of subjects having LDL pattern A. In contrast, in the cohort treated with 50 mg of Compound II, at 4 weeks and 8 weeks of treatment, the number of subjects having the less athrogenic pattern A increased from 8 to 24 and 25, respectively, with a similar drop in the number of pattern B. Treatment with 100 mg of Compound II had similar results with a large decrease in subjects having pattern B and an increase in the number of subjects having pattern A. These results were superior to a control group treated with the statin, Atorvastatin (LIPITOR).

TABLE I

| | Time | Pattern A | Pattern I | Pattern B |
|---|---|---|---|---|
| Placebo | Week 0 | 10 | 3 | 16 |
| | Week 4 | 11 | 4 | 13 |
| | Week 8 | 6 | 8 | 13 |
| MBX-8025 50 mg | Week 0 | 8 | 7 | 13 |
| | Week 4 | 24 | 0 | 3 |
| | Week 8 | 25 | 2 | 2 |
| MBX-8025 100 mg | Week 0 | 6 | 7 | 20 |
| | Week 4 | 25 | 4 | 1 |
| | Week 8 | 25 | 2 | 2 |
| Atorvastatin (ATV) 20 mg | Week 0 | 9 | 5 | 15 |
| | Week 4 | 12 | 6 | 10 |
| | Week 8 | 13 | 3 | 13 |
| MBX-8025 50 mg/20 mg ATV | Week 0 | 13 | 0 | 16 |
| | Week 4 | 26 | 3 | 0 |
| | Week 8 | 24 | 3 | 0 |
| MBX-8025 100 mg/20 mg ATV | Week 0 | 9 | 1 | 17 |
| | Week 4 | 25 | 1 | 1 |
| | Week 8 | 23 | 2 | 2 |

Figure 7:
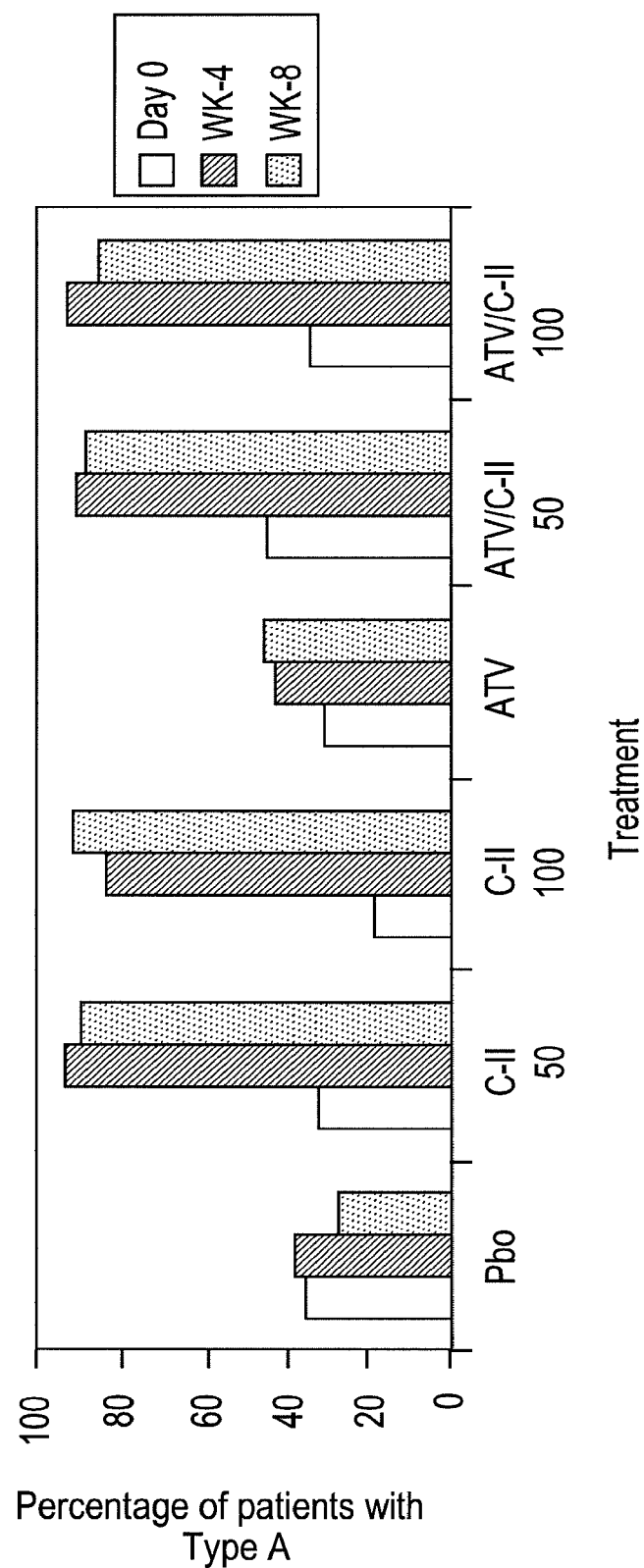
FIG. 7 illustrates the percentage of patients having LDL pattern A after various treatment regimens.
Figure 8:
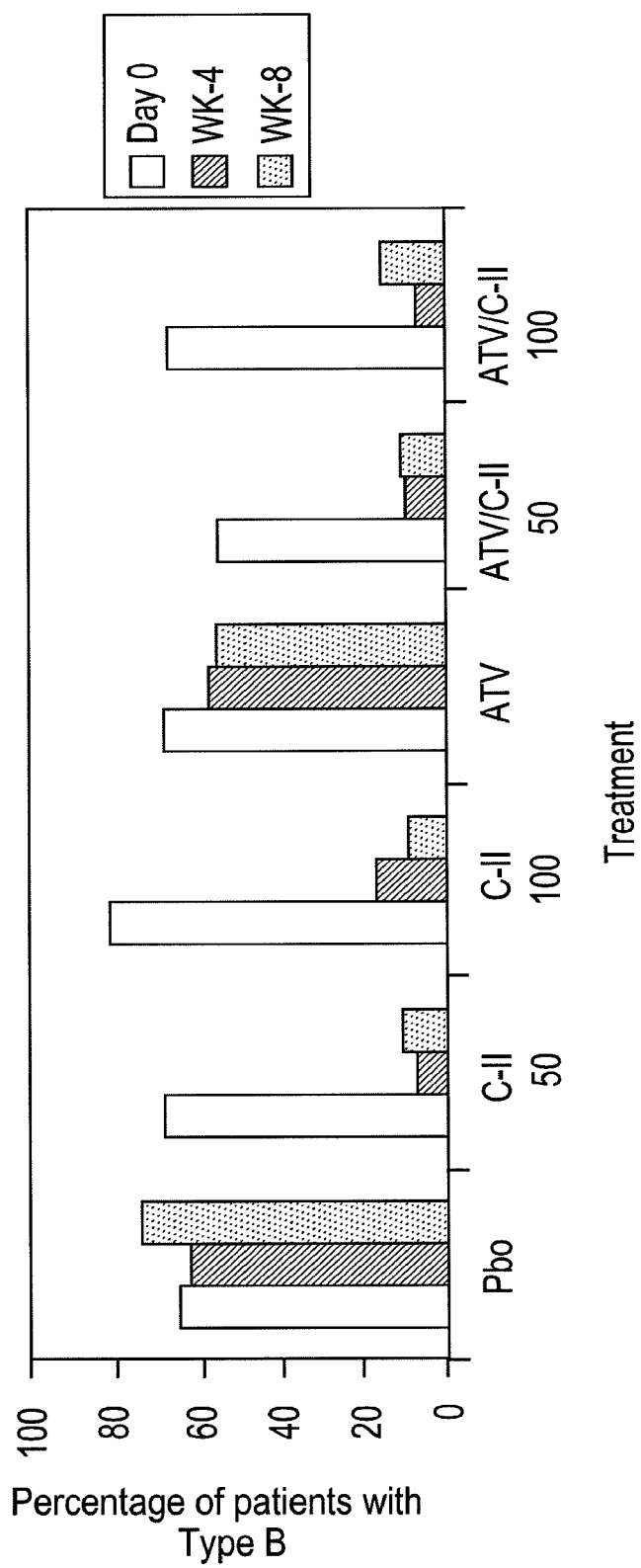
FIG. 8 illustrates the percentage of patients having LDL pattern B or I after various treatment regimens.

The above data is also summarized in FIGS. 7-8. FIG. 7 shows that the percentage of individuals having LDL pattern A went down over time when treated with a placebo but went up dramatically when Compound II was administered. FIG. 8 shows that the percentage of individuals having LDL pattern B went up over time when treated with a placebo but went down dramatically when Compound II was administered.

Figure 6:
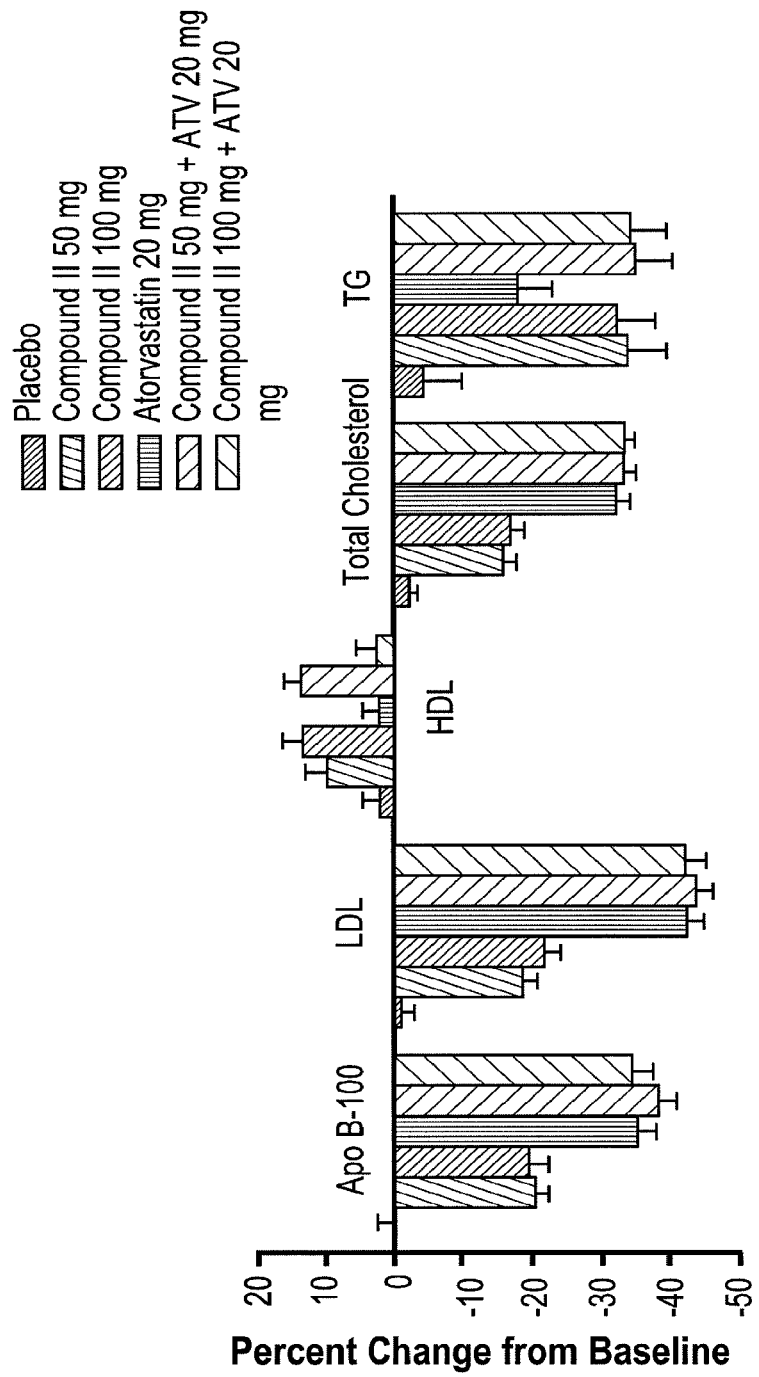
FIG. 6 summarizes the effect of Compound II on various blood components in obese subjects as described in the Example.

Results of various blood chemistry markers from this study are shown in FIG. 6. Among other things, these data show that Apo B-100, LDL, total cholesterol and triglycerides were reduced following administration with Compound II while HDL levels increased. This latter observation is interesting as Atorvastin had no effect of HDL levels. These data show that Compound II would be particularly beneficial to individuals who require or would otherwise benefit from an increase in HDL levels.

Example 2: Compound II Affects Cholesterol Synthesis

A series of experiments were performed to determine the effect of Compound II on cholesterol synthesis. Compound II was administered to human subjects and the effect on cholesterol ester, acyl-coenzyme A:cholesterol acyltransferase (ACAT) and Lecithin-cholesterol acyltransferase (LACAT) was determined after 21 days. The treatment decreased cholesterol concentrations in a dose-dependent fashion. The effect of treatment appeared similar between ACAT- and LCAT-derived cholesterol esters, indicating a reduction in cholesterol substrate.

Figure 9:
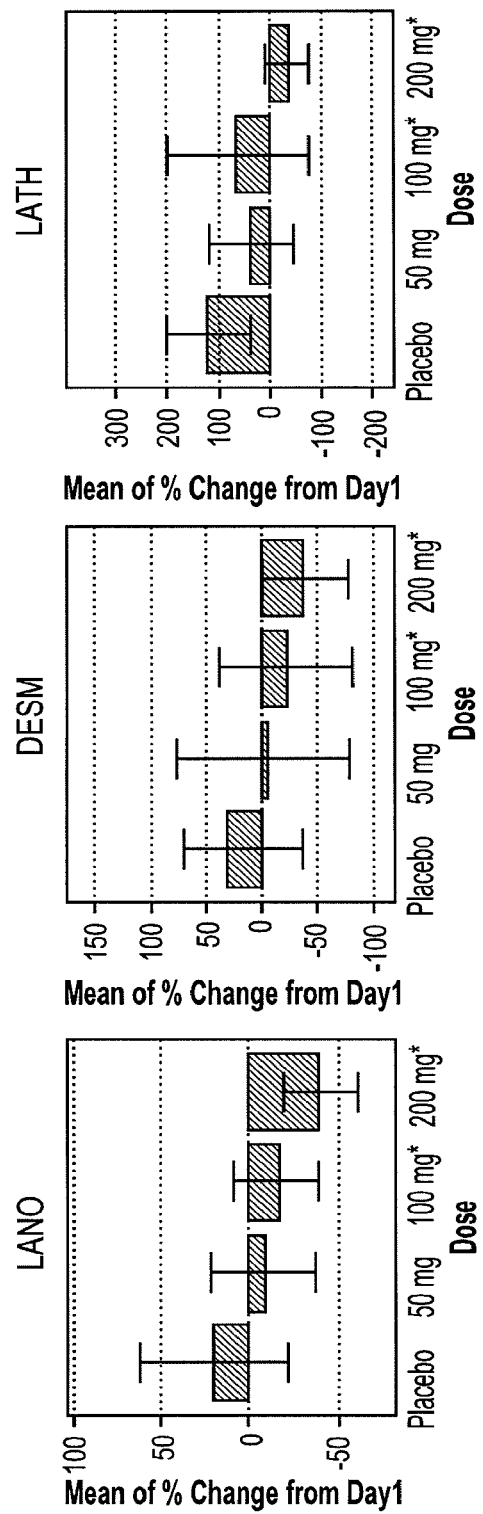
FIG. 9 illustrates quantity of lanosterol, desmosterol, and lathosterol (all cholesterol intermediates) in blood of individuals following administration of Compound II.

As shown in FIG. 9, Lanosterol, desmosterol and lathosterol are all major cholesterol synthesis intermediates and all decreased in a dose-dependent fashion indicating a decrease in cholesterol synthesis with treatment.

Example 3: Compound II Affects Cholesterol Absorption

This study was designed to examine the effect of Compound II on intestinal cholesterol absorption in mice using the fecal dual isotope ratio method. Eight-week-old male C57BL/6 mice were fed standard mouse chow (control) with no added cholesterol (Harlan Teklad diet T.8604) ad libitum. Mice were randomized into five groups: 1) control, water gavaged daily; 2) compound II gavaged daily (in water) at a dose of 3 mg/kg; 3) compound II gavaged daily (in water) at a dose of 10 mg/kg; 4) ezetimibe gavaged daily (in corn oil) at a dose of 5 mg/kg; 5) compound II fed daily as diet admix at a dose of approximately 15 mg/kg. Mice were housed individually and monitored daily for food consumption and body weight. Following eight days of feeding/drug administration, (and 1 hour following gavage of drug), nonfasted, unanesthetized animals were bled and plasma was isolated and flash-frozen at −80° C. for shipment and measurement of concentrations of Compound II and its metabolites. The following day (day 9), mice were gavaged with drug or control. One hour later, each mouse was gavaged with MCT oil containing [$^{14}$C]cholesterol and [$^{3}$H]sitostanol. Mice were housed individually in metabolic cages and ad libitum feeding and daily gavage of each drug was continued. Feces were collected daily from each animal for a period of 4 days. For each individual mouse, the 4-day feces were pooled, dried, saponified, extracted and counted.

Figure 10:
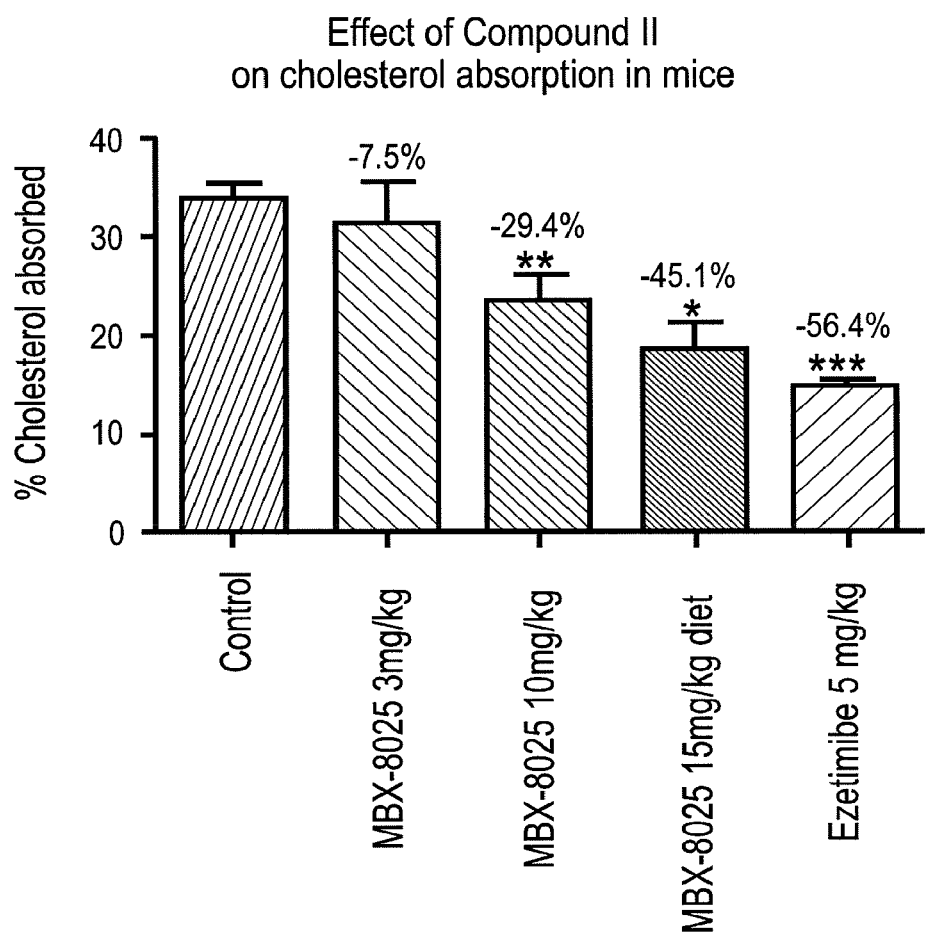
FIG. 10 illustrates the effect of Compound II on cholesterol absorption in mice following administration of Compound II.

Intestinal cholesterol absorption in age- and gender-matched C57BL/6 mice was determined by the fecal dual isotope ratio method. C57BLU6 control mice were found to absorb 33.9% of the [$^{14}$C]cholesterol. See, FIG. 10. Treatment with compound II by gavage at a dose of 3 mg/kg/d resulted in no significant change (−8%) in cholesterol absorption versus control. In contrast, treatment with compound II by gavage at a dose of 10 mg/kg/d resulted in a significant 29.4% reduction in cholesterol absorption versus control. Treatment with compound II as an admix to diet at an approximate dose of 15 mg/kg/d resulted in an even greater reduction in cholesterol absorption versus control (−45%, p<0.0006). This change was not significantly different from the 10 mg/kg/d dose. As a positive control, ezetimibe at a dose of 5 mg/kg/d resulted in a significant 56.4% reduction in cholesterol absorption (p<0.0000005). Statistical analysis between groups was assessed by unpaired Student's t-test. Statistical significance was defined as a two-tailed probability of less than 0.05.

Figure 11:
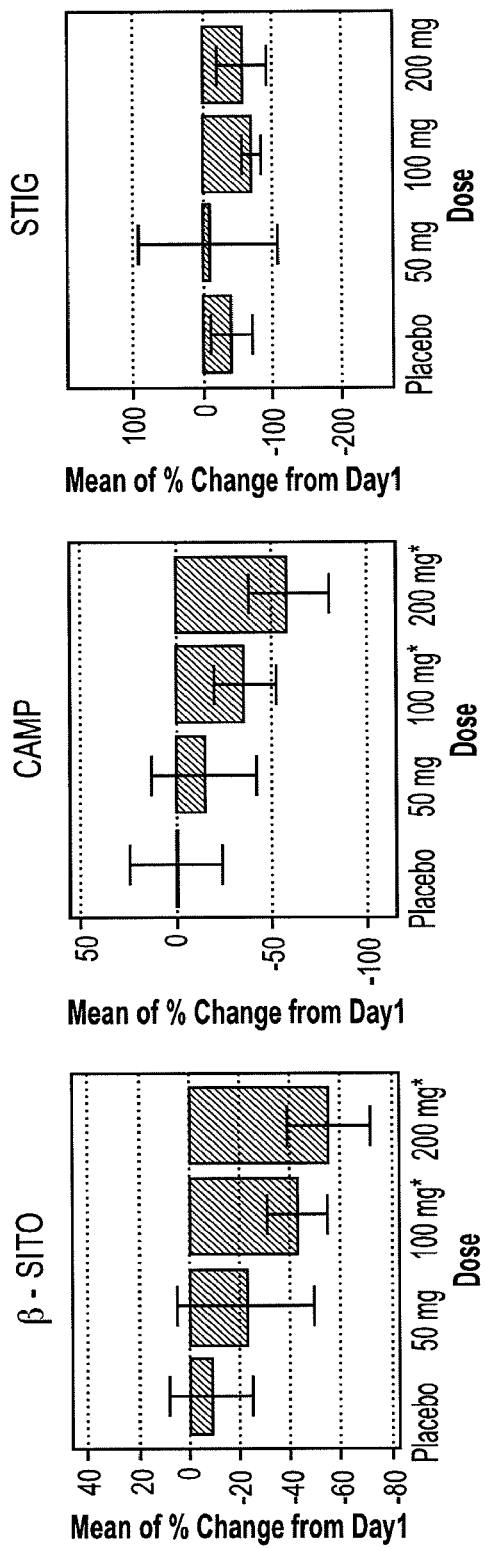
FIG. 11 illustrates the absorption of phytosterols in humans following administration of Compound II.

In another experiment, human subjects received an oral dose of Compound II at day 1 and daily thereafter and the effect of the drug was assessed on day 21. Phytosterols are poorly absorbed from diet, but are absorbed proportionally with dietary cholesterol and thus serve as good markers of cholesterol absorption. As shown in FIG. 11, β-sitosterol and campesterol were significantly decreased in a dose-dependent fashion indicating a decrease in cholesterol absorption with treatment. Stigmasterol was not significantly affected by treatment.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of changing the LDL particle size pattern in a human having LDL particle size pattern I or B, from pattern I to pattern A, or from pattern B to pattern I or A, comprising:
   (i) the identification of the human as having LDL particle size pattern I or B; and
   (ii) the administration to the human of a therapeutically effective amount of a compound of the formula

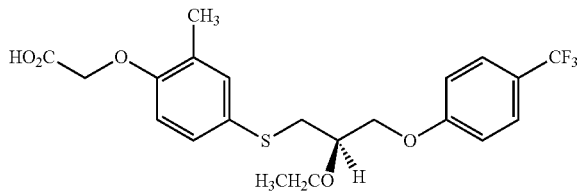

or a salt thereof;
thereby changing the LDL particle size pattern of the human from pattern I to pattern A, or from pattern B to pattern I or A.

2. The method of claim 1, where the human is identified as having an LDL particle size pattern B prior to administration of the compound.

3. The method of claim 2, where the human is identified as having an LDL particle size pattern I after administration of the compound.

4. The method of claim 1, where the human has diabetes.

5. The method of claim 1, where the human is insulin resistant.

6. The method of claim 1, where the human has atherosclerosis.

7. The method of claim 1, where the human has metabolic syndrome.

8. The method of claim 1, where the human has dyslipidemia.

9. The method of claim 1, further comprising administration to the human of a statin.

10. The method of claim 9, where the statin is atorvastatin.

* * * * *